(12) United States Patent
Becker

(10) Patent No.: US 8,436,141 B2
(45) Date of Patent: May 7, 2013

(54) **PURIFIED HEMOCYANIN OBTAINED FROM *FISSURELLA LATIMARGINATA*; SUBUNIT OF PURIFIED HEMOCYANIN; USE OF HEMOCYANIN, ITS SUBUNIT OR IMMUNOGENIC FRAGMENTS AND COMPOSITIONS CONTAINING THE SAME**

(75) Inventor: Maria Inés Becker, Santiago (CL)

(73) Assignee: Biosonda S.A., Santiago (CL)

( * ) Notice: Subject to any disclaimer, the term of this patent is extended or adjusted under 35 U.S.C. 154(b) by 362 days.

(21) Appl. No.: 12/418,222

(22) Filed: Apr. 3, 2009

(65) Prior Publication Data

US 2010/0255017 A1 Oct. 7, 2010

(51) Int. Cl.
*A61K 38/00* (2006.01)
(52) U.S. Cl.
USPC .......................................... 530/350; 514/1.1
(58) Field of Classification Search .................. None
See application file for complete search history.

(56) References Cited

U.S. PATENT DOCUMENTS

| | | | | |
|---|---|---|---|---|
| 5,855,919 A | * | 1/1999 | Ebert et al. | 424/547 |
| 6,852,338 B2 | * | 2/2005 | Oakes | 424/547 |
| 6,916,908 B2 | | 7/2005 | De Ioannes et al. | |

OTHER PUBLICATIONS

Amar et al, Aquaculture, 2005, 247(1-4):3-4.*
Morikawa et al, Ann Allergy, 1990, 65:415-417.*
Idakieva et al., "Spectroscopic Properties and Conformational Stability of *Concholepas concholepas* Hemocyanin", Journal of Fluorescence, Publisher: Springer Netherlands, ISSN: 1053-0509 (Print); 1573-4994 (Online); vol. 18, Nos. 3-4, Jul. 2008, Original Paper, pp. 715-725.
Becker et al., "Immunodominant role of CCHA subunit of *Concholepas* hemocyanin is associated with unique biochemical properties", International Immunopharmacology, vol. 9, Issue 3, Mar. 2009, pp. 330-339.
Gatsogiannis et al., "Keyhole limpet hemocyanin: 9-A CryoEM structure and molecular model of the KLH1 didecamer reveal the interfaces and intricate topology of the 160 functional units"; Journal of Molecular Biology; doi: 10.1016/j.jmb.2008.10.080; 385(3): 963-83.

* cited by examiner

*Primary Examiner* — Misook Yu
*Assistant Examiner* — Mark Halvorson
(74) *Attorney, Agent, or Firm* — Brinks Hofer Gilson & Lione; G. Peter Nichols

(57) ABSTRACT

The invention relates to purified hemocyanins, subunits or immunogenic fragments thereof, wherein the hemocyanins are purified from a hemolymph of *Fissurella latimarginata* (black limpet), *Fissurella cumingi* (strawberry limpet), or *Fissurella maxima* (queen limpet). The invention also relates to compositions including the purified hemocyanins and methods of treating neoplastic diseases by administering such compositions.

9 Claims, 17 Drawing Sheets

PURIFIED HEMOCYANIN OBTAINED FROM *FISSURELLA LATIMARGINATA*; SUBUNIT OF PURIFIED HEMOCYANIN; USE OF HEMOCYANIN, ITS SUBUNIT OR IMMUNOGENIC FRAGMENTS AND COMPOSITIONS CONTAINING THE SAME

BACKGROUND

The present invention relates to methods of isolating hemocyanins from hemolymph of three Chilean species of limpet. Specifically, the present invention relates to hemocyanins obtained from hemolymph of *Fissurella latimarginata, Fissurella cumingi* and *Fissurella maxima*.

Hemocyanins are proteins whose function is oxygen transport in several mollusk and arthropod species. These proteins contain copper, which confers the characteristic blue colour after binding with oxygen. Hemocyanins of mollusks and arthropods are useful in various applications in immunology, immunochemistry and biotechnology, because they are effective immunogens inducing the synthesis of large amounts of specific antibodies and the activation of T-lymphocytes. Some of the applications of hemocyanins include: 1) their use as experimental antigens in studies of the immune response of vertebrates, 2) their use as carrier proteins used in the production of monoclonal and polyclonal antibodies against different substances, which by themselves are not immunogenic (haptens) such as synthetic peptides, recombinant proteins of microorganisms, plants, animals and humans, toxins, medications, hormones, drugs and chemicals (antibodies generated can be used in the production of kits for diagnosis, organic molecule screening and therapies for animals and humans diseases), 3) their use as a non specific immunostimulating agent in the therapy of certain types of cancer, and 4) their use as a diagnosis reagent for diseases caused by parasites, such as Schistosomiasis.

The most frequent use of hemocyanins, particularly hemocyanin from the keyhole limpet or KLH (*Megathura crenulata*), is in biomedicine and biotechnology, as a carrier protein to develop antibodies against peptides and haptens of diagnostic interest, such as toxins, hormones, drugs and chemicals from different origin. The main clinical use of KLH is as a non-specific immunostimulanting agent in the treatment of surface bladder carcinoma.

Hemocyanin present in hemolymph of some mollusks has a high immunogenic capability in vertebrates due to its high molecular weight (from $4.5 \times 10^6$ to $1.4 \times 10^7$), its phylogenetic origin far from vertebrates and also, because it is a glycoprotein.

The basic structure of hemocyanins is made up by subunits arranged forming a decamer (see FIG. 1). In gastropods, decamers are normally associated, forming di-decamers, conferring on them a D5 simmetry, which can be considered similar to that of viruses. This molecule contains a large amount of ε-amine groups of lysins, which allow their conjugations with other proteins and haptens. Conjugation is performed through traditional methods based on carbodiimide or glutaraldehyde or hydroxysuccinimide esters. A hemocyanin molecule commonly accepts up to about 100 hapten molecules without lossing its immunogenicity.

W. O. Weigle ("Immunochemical Properties of Hemocyanin", Immunochemistry. vol. 1, pp. 295-302, 1964) teaches the immunochemical properties of hemocyanin obtained from *Megathura crenulata*, but also demonstrates that the preparation used contained at least two antigenic components, according to results obtained by gel difussion, immunoelectrophoresis and cellulose acetate electrophoresis.

J. E. Mellema and A. Klug ("Quaternary Structure of Gastropod Hemocyanin". Nature vol. 239, pp. 146-150, 1972) demonstrated the presence of a quaternary structure in hemocyanins obtained from three different gastropods (*Kelletia kelletia, Busycon canaliculatum* and *Helix pomatia*). For all of them, hemocyanins form cylindrical particles, with no basic structual differences found. Variations seem to reflect differences due to preparations methods.

H. B. Herscowitz et al. ("Immunochemical and Immunogenic Properties of Purified Keyhole Limpet Hemocyanin", Immunology. vol. 22, pp. 51-61, 1972) described a method of obtaining a relatively homogeneous preparation of *Megathura crenulata's* hemocyanin. The procedure described by Herscowitz et al. included the use of ion-exchange cromatography in DEAE-cellulose, followed by agarose-bead gel filtration. The product obtained was analized through agar immunoelectrophoresis, polyacrilamide gel electrophoresis and agar double diffusion, showing that the purified preparation contained just one primary antigenic component, but the raw material contained multiple antigenic components.

J. Markl et al. ("The role of two distinct subunit types in the architecture of keyhole limpet hemocyanin (KLH), Naturwissenschaften. vol 78, pp. 512-514, 1991), through transmission electronic microscopy with negative staining, ultracentrifugation, dissociation in adequate buffers and the subsequent native polyacrilamide gel chromatography, demonstrated that hemocyanin from *Megathura crenulata* contains two types of molecules: one made up of 8 functional units named type-1 and the other made up by 7 functional units, named type-2.

J. R. Harris et al. ("Immunoelectron microscopy of hemocyanin from the Keyhole Limpet (Megathura crenulata): A parallel subunit model", Journal of Structural Biology. vol 111, pp. 96-104, 1993) used anti-hemocyanin monoclonal antibodies from *Megathura crenulata* in transmission electronic microscopy with negative staining and found that, within each decamer, exist a parallel array of subunits.

R. D. Swerdlow et al. ("Keyhole limpet hemocyanin: structural and functional characterization of two different subunits and multimers", Comparative Biochemistry and Physiology. vol 113B, pp. 537-548, 1996) demonstrated through immunoelectrophoresis analysis that both molecular forms described for hemocyanin (KLH1 and KLH2) do not include common epitopes and differ with regard to the immune response induced in experimental animals.

S. M. Sóhngen et al. ("Mass determination, subunit organization and control of oligomerization states of keyhole limpet hemocyanin (KLH)", European Journal of Biochemistry. vol 248, pp. 602-614, 1997) studied the structure of KLH1 and KLH2 through analytical scanning electronic microscopy, polyacrilamide gel electrophoresis, immunoelectrophoresis, controlled proteolytic digestion and amino acid sequencing. They found that these functional subunits differ both in size and in the preferential aggregation form. KLH1 and KLH2 were found to have a molecular mass of 400 KDa and 345 KDa, respectively. The subunit of KLH1 was found to have 8 different functional domains of 45 to 65 Da. In contrast, subunit KLH2 was found to have 7 functional domains and to lack the C-terminal domain named 1h, present in KLH1. In addition, KLH subunits differed with regard to the association and dissociation rates.

C. A. Olsson et al. ("Immunologic reduction of bladder cancer recurrent rate", Journal of Urology Vol. 111, pp 173-176, 1974) looked at a non-specific immunostimulation with Keyhole limpet hemocyanin in 29 patients (26 men and 3 women, between 30 to 93 year range, naive for radiotherapy or chemotherapy) diagnosed with transitional surface bladder carcinoma. Specifically, patients were divided in two groups, according to the disease background. Group 1, included 10 patients with 13 bladder tumor episodes receiving hemocyanin 5 mg subcutaneously at the study initiation. Group 1 was considered the control group, because the 2-year tumor frequency before the treatment is known. Group 2 included 19 newly diagnosed patients (1 year), who were treated through transurethral resection only. 9 patients in Group 2 were immunized with hemocyanin and 10 were not, comprising the control group. A significant reduction of frequency in tumor recurrence in a 2-year follow-up period was found in both of hemocyanin-treated patients.

C. D. Jurincic et al. ("Immunotherapy in bladder cancer with Keyhole-limpet hemocyanin: A randomized study", Journal of Urology. vol 139, pp 723-726, 1988) presented results from two studies aimed to assess the immunotherapeutic effect of the Keyhole limpet hemocyanin in patients diagnosed with surface bladder cancer. The first study began in 1982 and involved 44 patients undergoing recurrent surface bladder cancer surgery. Previous to therapy through vesical instillation with hemocyanin, patients were immunized with hemocyanin 1 mg intracutaneously and received 10 mg monthly by vesical instillation. The control group was given mitomycin C 20 mg monthly. Out of 21 patients treated with hemocyanin, 20 (95.2%) showed partial and complete prevention of the tumor and 3 (14.2%) showed tumor recurrence, compared with 9 (39.1%) of the control group. The second study began in 1984 with 81 patients given the same treatment as the previous study. No control group was present in the follow up study. 17 Patients (20.9%) were found with tumor recurrence and 70 patients (86.4%) showed partial and full prevention. In patients treated with Keyhole limpet hemocyanin, no local or systemic adverse effects were found. These studies have been complemented with C. D. Jurincic et al. (Effect of keyhole limpet hemocyanin (KH) and bacillus Calmette-Guerin (BCG) instillation on carcinoma in situ of the urinary bladder. Anticancer Res. 1995;15:2771-2776) and C. D. Jurincic et al. (Keyhole limpet hemocyanin for carcinoma in situ of the bladder: a long-term follow-up study. Eur. Urol. 2000;37 Suppl 3:45-9), who have provided further evidence regarding immunotherapy of surface bladder cancer using keyhole limpet hemocyanin.

J. Flamm et al. ("Recurrent superficial transitional carcinoma of the bladder: Adjuvant chemoherapy versus immunotherapy. A prospective randomized trial", Journal of Urology, vol 144, pp.260-263,1990) presented results of a comparative study on prevention and treatment of the transitional bladder cancer standard therapy with etoglucids versus immunotherapy with Keyhole-limpet hemocyanin in 84 patients with high-risk tumor recurrence. Before the instillation started, all patients were subjected to a tumor transurethral removal and, therefore, were tumor-free at the time of treatment initiation. The group of patients treated with etoglucids received 0.565 mg weekly over 6 weeks and then monthly for 1 year. The group of patients treated with hemocyanin was immunized with 1 mg intracutaneously and then received vesical instillations 30 mg each over 6 weeks and then monthly for 1 year. The recurrence rate was 60.9% in patients treated with etoglucid versus 55.3% in patients treated with hemocyanin. The difference between both treatments was not significant, concluding that immunotherapy of this kind of recurrent tumors with hemocyanin is comparable in efficacy to the standard treatment.

D. L. Lamm et al. ("Immunotherapy of murine bladder cancer with Keyhole Limpet hemocyanin (KLH)" Journal of Urology. vol. 149, pp. 648-652, 1993) provided results from immunotherapy with Keyhole limpet hemocyanins in a bladder cancer experimental model in mice of the C3H/HeN strain implanted with MBT2 cells, demonstrating that hemocyanin is an immunomodulator with significant antitumoral activity in this animal model. Recently, D. L. Lamm et al. (Keyhole limpet hemocyanin immunotherapy of bladder cancer: laboratory and clinical studies. Eur Urol. 2000;37 Suppl 3:4144) developed immunotherapy with Keyhole-limpet hemocyanin in humans through laboratory and clinical studies.

M. M. Wishahi et al. (Keyhole limpet hemocyanin immunotherapy of bladder cancer: A new treatment modality? phase 11 trial: Superficial bladder cancer", Journal of Urology. Vol 153, pp. 926-928, 1995) provided results of treatment with Keyhole limpet hemocyanin of 13 patients presenting with transitional bladder tumors associated with urinary schistosomiasis. Immunotherapy with hemocyanin was found to reduce tumoral recurrence rate to 15.4% compared to 76.9% before therapy.

It was also demonstrated that Keyhole limpet hemocyanin has both adjuvant and immunostimulant properties. As such, hemocyanin compounds are referred to as immunomodulators. J. Banchereau el al. (Immune and clinical responses in patients with metastatic melanoma to CD34(+) progenitor-derived dendritic cell vaccine. Cancer Res. 2001;61:64518) and P Hersey et al. (Phase 1/II study of treatment with dendritic cell vaccines in patients with disseminated melanoma. Cancer Immunol. Immunother. 2004;53:125-34) demonstrated the use of Keyhole limpet hemocyanin as immunomodulator in the treatment of disseminated melanoma. In particular, the group applied hemocyanin as immunomodulator for therapy against melanoma through dendritic cells loaded with a tumor extract.

Based on the state of the art, traditionally in all the above mentioned studies, the hemocyanin drawn from the Keyhole Limpet has been used, which corresponds to the mollusk *Megathura crenulata*, whose haemocyanyn is known as KLH.

Another form of hemocyanin includes hemocyanin obtained from the Chilean mollusk "Loco" (*Concholepas concholepas*), named CCH (De Ioannes & cols., (2004). Hemocyanin of the mollusk *Concholepas concholepas* exhibits an unusual heterodecameric array of subunits (J. Biol. Chem., 279, 26134-42. ) and shows immunostimulant properties similar to KLH, used for generation of monoclonal and policlonal antibodies. In particular, it was shown previously that hemocyanin from *Concholepas concholepas* has two subunits exhibiting different behaviors, showing that the subunit CCH-A is more immunogenic than subunit CCH-B (De Ioannes & Becker, 2005, US Patent 2005/0020486 A1).

Over-exploitation of Keyhole Limpet has created a KLH shortage in the international market, and the encouraging results of immunostimulation and immunotherapy of bladder cancer in humans, have driven the search for molecules with similar characteristics.

From the above stated, the need for alternative substances to replace or complement the use of KLH, complying with proper characteristics related to the immune response, becomes evident.

SUMMARY

The present invention relates to hemocyanins obtained from hemolymph of three Chilean species of limpet, in particular *Fissurella latimarginata, Fissurella cumingi* and *Fissurella maxima*.

Specifically, the inventors demonstrated that every purified hemocyanin of these limpets has, surprisingly, an immunogenicity higher than hemocyanins of other gastropods described in the literature, including KLH and CCH. This characteristic is further noted in the case of purified hemocyanin from *Fissurella latimarginata*.

For purposes of the present specification and claims, hemocyanin purified from hemolymph of *Fissurella latimarginata* is referred to as FLH; hemocyanin purified from hemolymph of *Fissurella cumingi* is referred to as FCH; and hemocyanin purified from hemolymph of *Fissurella maxima* is referred to as FMH.

BRIEF DESCRIPTION OF THE DRAWINGS

FIG. 1A shows and image of gastropod hemocyanin obtained through negative dye on TEM. The insert shows a side view molecule (rectangle) and other from top (circle). The bar indicates 100 nm length. FIG. 1B shows a model for gastropod hemocyanin structure where i. is a Didecamer (8-9 Ma), ii. is a Decamer (10 subunits), iii. is a Subunit (450-500 KDa) and iv. shows functional units (FUs, 45-50 KDa).

FIG. 2A shows *Fissurella latimarginata*. FIG. 2B shows *Fissurella cumingi*. FIG. 2C shows *Fissurella maxima*. The photographs show an aspect of the animals and the foot area, where hemolymph is drawn. In the insert, a diagram is shown pointing out physical differences among the three species (from Oliva and Castilla, 1992).

FIG. 3A shows hemocyanin precipitated at 50% with ammonium sulphate (bottle 250 ml). FIG. 3B shows the final product after the dyalisis against the stabilizing buffer. The volume of dialysed hemocyanin from left to right corresponds to about 200 mL (*Fissurella latimarginata* and *Fissurella cumingi*) and 300 ml (*Fissurella maxima*).

FIG. 4A shows FCH and the insert shows a detailed aspect of a didecamer side view (long arrow), top view (arrow head) and aspect of a decamer (short arrow). FIG. 4B shows FLH. FIG. 4C shows FMH and the arrow indicates a multimer. At the bottom of every microscope photograph, the magnification is identified.

FIG. 5A shows agarose gel electrophoresis under native conditions. 4 pg of hemocyanin were loaded per track. The electrophoresis run time was 4 hours, at 35 Volts. FIG. 5B shows polyacrylamide gel electrophoresis under dissociating native conditions. 20 ug of each hemocyanin per track were loaded, previously incubated in the electrophoresis buffer for dissociating native conditions for 24 hours at 4° C. The electrophoresis run time was 24 hours at 100 Volts. FIG. 5C shows electrophoresis under denaturating conditions and reducing conditions (SDS-PAGE), on polyacrylamide gels. 5 ug of each hemocyanin per track was loaded, previously incubated in the loading buffer for electrophoresis under reducing denaturating conditions for 5 minutes at 100° C. The electrophoresis was run 1 hour at 35 Volts, followed by 3 hours at 95 Volts. Figure % D shows electrophoresis under denaturating conditions, non reducing SDS-PAGE, on polyacrylamide gel. 2 ug of each hemocyanin per track was loaded, incubated in a sample buffer for electrophoresis under non reducing denaturating conditions over 5 minutes at 100° C. The electrophoresis was run 1 hour at 35 Volts, followed by 3 hours at 95 Volts. All gels were stained with Coomassie blue.

FIG. 7A is FLH, Figure &B is FMH and FIG. 7C is KLH.

FIG. 9A shows the anti-FLH response. FIG. 9B shows the anti-FCH response. FIG. 9C shows the anti-FMH response. FIG. 9D shows the anti-CCH response. FIG. 9E shows the anti-KLH response. The plate was activated with 1 ug of each protein by well, was blocked by a non-related protein, and then was incubated with the homologous serum. Later, it was incubated with an anti-IgG of mouse conjugate developed in goat and conjugated with alkaline phosphatase. Finally, it was developed with pNPP. OD was measured at 405 nm.

FIG. 10A shows BALB/c. FIG. 10B shows C57BL/6. FIG. 10C C3H/He. The relative absorbance value was obtained giving value one to the highest absorbance recorded per hemocyanin for each strain.

FIGS. 11A and 11D show the staining control of proteins in the gel using Coomassie blue. FIG. 11B shows the cross reaction of hemocyanins with anti FLH serum. FIG. 11C shows the cross reaction of hemocyanins with anti FCH serum. FIG. 11E shows the cross reaction of hemocyanins with anti FMH serum. FIG. 11F shows the cross reaction of hemocyanins with anti CCH serum. FIG. 11G shows the cross reaction of hemocyanins with anti KLH serum.

DETAILED DESCRIPTION

Figure 1:
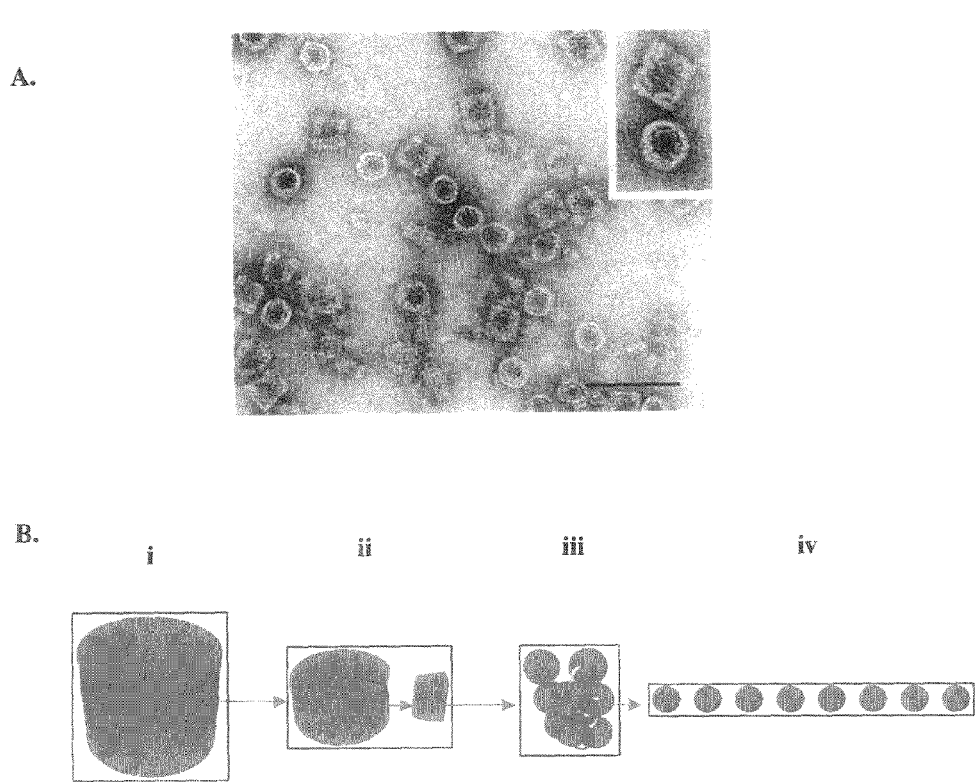
FIG. 1 shows shows the gastropod hemocyanin structure. In particular.

The present invention relates to purified hemocyanins, subunits or immunogenic fragments thereof, where the hemocyanins are purified from hemolymph of *Fissurella latimarginata* (black limpet), *Fissurella cumingi* (strawberry limpet) or *Fissurella maxima* (queen limpet). Hemocyanin purified from hemolymph of *Fissurella latimarginata* is FLH;

hemocyanin purified from hemolymph of *Fissurella cumingi* is FCH; and hemocyanin purified from hemolymph of *Fissurella maxima* is FMH.

In an embodiment of the invention, the hemocyanin obtained from *Fissurella latimarginata* comprises didecamers made up of just one kind of subunit and shows about the following dimensions: diameter of about 325 Å, height of about 268 Å, and width of about 362 Å. This hemocyanin has immunogenicity higher than that of other gastropod hemocyanins.

In another embodiment of the invention, the hemocyanin obtained from *Fissurella cumingi* comprises didecamers made up of just one kind of subunit and shows about the following dimensions: diameter of about 339 Å height of a bout 280 Å, and width of about 350 Å.

In a further embodiment of the invention, the hemocyanin obtained from *Fissurella maxima* comprises didecamers, made up of just one kind of subunit and shows about the following dimensions: diameter of about 363 Å, height of about 287 Å, and width of about 380 Å.

In an embodiment of the invention, the subunit obtained from *Fissurella latimarginata*, *Fissurella cumingi* or *Fissurella maxima* has a relative molecular mass about 353 KDa and a characteristic Raman SERS profile inherent to each of them.

The invention also relates to use of the hemocyanins, subunits or immunogenic fragments thereof in preparation of an immunostimulant or immunomodulator medication, preparation of an adjuvant for vaccines, as well as hapten- or peptide-carrier protein, or preparation of a product for diagnosing immunocompetence.

In another embodiment of the invention, the immunostimulant medication may be used in therapy against neoplastic diseases.

In yet another embodiment of the invention, the immunomodulator medication may be used in therapy against neoplastic diseases by targeting dendritic cells loaded with a tumor extract.

In a particular embodiment of the invention, the immunostimulant or immunomodulator medication is used for therapy against neoplastic diseases, such as cervical cancer, head and neck cancer, transition cell cancer of renal pelvis and ureter, cancer of colon, rectum and anus, bile duct cancer, neck cancer, esophagus cancer, gastric cancer, liver cancer, bone cancer, adrenocortical cancer, salivary gland cancer, hypopharynx cancer, larinx and hypopharynx cancer, ovarian cancer, vaginal cancer, vulva cancer, uterine endometrium cancer, Gestational trophoblastic tumors, nasopharinx cancer, oropharinx cancer, parathyroid cancer, urethra cancer, bladder cancer, pancreatic cancer, penis cancer, skin cancer, prostate cancer, lung cancer, kidney cancer, breast cancer, male breast cancer, testis cancer, thymus cancer, thyroid cancer, unknown primary tumor cancer, small intestine cancer, oral lip cancer, prenatal sinus and nasal cavity cancer, metastatic cancer, childhood cancer, islet cell carcinoma, Merkel cell carcinoma, Pheochromocytom, Leukemia, Lymphoma, Hodgkin's lymphoma, no-Hodgkin's lymphoma, AIDS-related Lymphoma, intraocular melanoma, Mesotelioma, Fungoid mycosis, Mieloma, plasmatic cell neoplasma, Neuroblastoma, Osteosarcoma, Retinoblastoma, Swing' Sarcoma, Kaposi' Sarcoma, Sarcomas, Sezary' Síndrome, Myelodysplastic syndrome, mieloprolipherative disorders, Wilms' tumor, gastrointestinal carcinoid tumors, brain tumors, germinative cell tumors, pituitary gland tumors, or eye tumors.

In another embodiment of the invention, the hemocyanin, subunits or immunogenic fragments thereof may be used as a hapten- or peptide-carrier protein to produce antibodies or may be used in production of vaccines.

Further, the invention relates to a pharmaceutical composition comprising hemocyanin, or its subunits or immunogenic fragments, and a suitable vehicle for immmunization of vertebrates.

The invention relates to compositions comprising purfied hemocyanin, subunits or immunogenic fragments thereof in an amount sufficient to provide an effective immunostimulant or immunomodulator activity, wherien the hemocyanin is purified from hemolymph of *Fissurella latimarginata* (black limpet), *Fissurella cumingi* (strawberry limpet) or *Fissurella maxima* (queen limpet).

In certain embodiments, these compositions may be used for treatment of neoplastic diseases. For example, neoplastic diseases may be treated by targeting dendritic cells loaded with tumor extract. Various methods of adminstering compositions for treatment of neoplastc diseases are known and can be used to adminster the hemocyanin.

In an embodiment of the invention, the composition comprises between about 1 and about 500 mg/mL hemocyanin, and a suitable vehicle for use in immunization of vertebrates.

In other embodiment of the invention, the composition comprises between about 5 and about 30 mg/mL hemocyanin, and a suitable vehicle for use in immunization of vertebrates.

Further, the invention relates to a method of treating neoplastic diseases. The method includes the step of administering to a patient an effective amount of purified hemocyanin, its subunits or immunogenic fragments purified from hemolymph of *Fissurella latimarginata* (black limpet), *Fissurella cumingi* (strawberry limpet) or *Fissurella maxima* (queen limpet).

In certain other embodiments, the invention relates to a method for inducing an immune response in a patient. The method includes the step of administering a composition comprising a purified hemocyanin, or subunits or immunogenic fragments thereof, in an amount sufficient to provide an effective adjuvant effect, wherein the hemocyanin is purified from a hemolymph of *Fissurella latimarginata* (black limpet), *Fissurella cumingi* (strawberry limpet), or *Fissurella maxima* (queen limpet); and an antigen.

It should be noted that references to "an", "one", or "various" embodiments in this disclosure are not necessarily to the same embodiment, and such references contemplate more than one embodiment.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The recitation of "about" or "substantially" used with reference to a quantity, such diameter, includes variations in the recited quantity that are equivalent to the quantity recited, for instance an amount that is insubstantially different from a recited quantity for an intended purpose or function.

The term "antibody" refers to an immunoglobulin, derivatives thereof that maintain specific binding ability, and proteins having a binding domain that is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE.

The term "adjuvant" refers to a compound added to a composition comprising an antigen, to increase an antigen's intrinsic immunogenicity. An adjuvant may be administered simultaneously with the antigen. An adjuvant and the antigen may be administered at the same site. Alternatively, an adjuvant may be administered at a site different from the site that the antigen is administered.

The term "antigen" refers to a molecule whose shape triggers the production of antibodies that will bind to the antigen. An antigen is a foreign substance capable of triggering an immune response in an organism.

The term "immunostimulant" refers to a compound that by itself stimulates the immune system with benefits to a patient.

The term "immunomodulator" refers to a compound having both, adjuvant and immunostimulant properties.

The term "immunogenicity" refers to the ability of a compound to induce the immune response in vertebrates.

The term "carrier protein" refers to a protein with haptens attached, i.e., small-size compounds that by themselves are not immunogenic. In other words, the carrier protein does not itself induce a physiological response, e.g., an immune response. Preferably, the carrier protein does not result in any adverse or undesired side effects and/or does not result in undue toxicity. Preferably the carrier protein is a pharmaceutically acceptable carrier protein.

The term "purified" in connection with the phrase "purified hemocyanine" refers to a series of processes intended to isolate a single type of hemocyanine from a complex mixture. Protein purification is vital for the characterization of the function, structure and interactions of the protein of interest. The various steps in the purification process may free the protein from a matrix that confines it, separate the protein and non-protein parts of the mixture, and finally separate the desired protein from all other proteins. A specific purification process for hemocyanines is described in detail below.

The following examples illustrate some specific embodiments of the invention, but they are not intended to limit the context or scope of the present invention.

EXAMPLES

Example 1

Extraction and Purification of Hemocyanins from Limpet Hemolymph

Methods
A. Hemolymph Extraction

Live specimens of *Fissurella latimarginata* (black limpet), *F. cumingi* (strawberry limpet) and *F. maxima* (Queen limpet) were harvested from the Quintay Bay, V$^{th}$ Region of Chile, and brought alive in seawater to Biosonda in Santiago. The specimens were kept on ice for 1 hour; some of their anatomical charateristics, such as weight and size, were recorded. The hemolymph extraction was made through the animal's foot by incisions at room temperature (Gebauer et al., 1994), under germ-free conditions. Some hemolymph characteristicis, such as color, collected volume per species and pH were recorded.

B. Hemocyanin Purification

Purification of hemocyanins from hemolymph was performed through precipitation with 50% saturated ammonium sulphate. Hemocytes and other hemolymph cells were removed by centrifugation at 2,400 rpm in the IEC CENTRA-7R centrifuge for 20 minutes at 4° C. The supernatant with the hemocyanin suspension was recovered. Precipitation was made by slow addition and stirring of ammonium sulphate crystals to reach a 50% saturation at 4° C. over 12 hours. After this period, the solution was centrifuged at 10,000 rpm for 1 hour at 4° C. in the Sorvall centrifuge; all the supernatant was removed. The precipitate was resuspended in a stabilizing buffer. This procedure of concentration and precipitation was repeated twice more. The resuspended precipitate was dialized at 4° C. against the stabilizing buffer to remove ammonium sulphate and leave hemocyanins resuspended in the buffer. The hemocyanin solution was clarified by centrifugation at 10,000 rpm for 1 hour at 4° C. in the Sorvall centrifuge. Later, the dialized protein was filtered using a 0.22 um Stericup Milli pore Express™ Plus, under germ-free conditions. Aliquots were made under laminar flow hood in 10-mL sterile vials at 4° C. The protein concentration was determined using the reagent Coomassie Plus Protein (Bradford's method) according to the manufacturer's instructions.

C. Biochemical Characterization of Purified Limpet Hemocyanins

Structural Analysis Through Transmission Electronic Microscope

The general procedure described by Fernández-Morán et al.(1966) was used with modifications (De Ioannes et al., 2004). Specifically, 10-µl sample aliquots were obtained (1 mg/ml) and placed on copper grids covered with Parlodion 3% in amyl acetate. Later, the sample was stained for 1 minute with previously filtered, 10 ul uranyl acetate solution 2%. The grids were dried in a moisture-free room at room temperature overnight and observed under an electronic microscope Phillips Tecnai 12 at the Servicio de Microscopia Electrónica of the Pontificia Universidad Católica de Chile.

D. Analysis of Polypeptide Composition Through Various Types of Electrophoresis

Electrophoresis Under Native Conditions 15 g of agarose were dissolved in 100 mL of electrophoresis buffer for native conditions. Later, 4 ug from each hemocyanin solution was drawn and dissolved in loading buffer for electrophoresis. Gels were dissolved in an horizontal electrophoresis chamber, using the same above-mentioned buffer. The electrophoresis time was 4 hours, keeping a potential difference of 35 volts. The later process consisted of fixing the proteins to gel (methanol 50% v/v, acetic acid 12% v/v) for 15 minutes and gentle stirring. Following the fixation step, protein staining was performed (methanol 50% v/v, acetic acid 10% v/v, Coomassie blue R-250 0.05% v/v) for further 15 minutes with gentle stirring. Finally, the gels were left destaining overnight in the destaining solution for gels (methanol 30% and acetic acid 7%).

Electrophoresis Under Dissociative Native Conditions

The method of Swerdlow y cols was used (1996) with modifications. Before electrophoresis, the hemocyanin samples were incubated in the loading buffer for 1 hour at 4° C. Later, 20 ug of dissociated protein were loaded in polyacrylamide gels with a 3-7% gradient resolutive phase and 4% concentrating phase in acrilamide. Alternatively, just one polyacrylamide gel 5-10% was used. Gels were run in a vertical electrophoresis chamber, using electrophoresis buffer for dissociating native conditions. The electrophoresis run time was 24 hours, keeping a potential difference of 100 volts. The later process consisted of fixing proteins to gel, as described earlier.

Electrophoresis Under Denaturating Conditions, Reducing SDS-PAGE

The method described by Laemmli (1970) was used with minor modifications. 5 ug of protein were dissolved in loading buffer for electrophoresis under reducing denaturating conditions, and incubated in a water bath at 100° C. during 5 minutes. Later, the mixture was loaded on polyacrylamide gels with a gradient separating phase 3-7% and a concentrating phase 3% in acrilamide. Gels were set up in a vertical electrophoresis chamber, using electrophoresis buffer for denaturating conditions. The electrophoresis run time was 1 hours, keeping a potential difference of 35 volts, followed by 3 hours at 95 volts. The later process consisted of fixing proteins to gel, as described earlier.

Electrophoresis Under Denaturating Conditions (Non-Reducing SDS-PAGE)

The method described by Laemmli (1970) was used with minor modifications. 2 ug of protein were incubated in sample buffer for electrophoresis under non-reducing denaturating conditions for 5 minutes at 100° C. and loaded on polyacrylamide gels with a gradient separating phase 38% and a concentrating phase 4% in acrilamide. Gels were stup in a vertical electrophoresis chamber, using electrophoresis buffer for denaturating conditions. The electrophoresis run time was 1 hour, using 35 volts, followed by 3 hours at 95 volts. Later, fixing of the proteins to gel and staining was performed as described earlier for electrophoresis under native conditions.

Capillary Eletrophoresis (EC)

Separation of subunits by capillary electrophoresis was made with the collaboration of Dra. Maria Antonieta Valenzuela, Departamento de Bioquímica y Biología Molecular, Facultad de Ciencias Químicas y Farmacéuticas of the Universidad de Chile. The equipment used was an Analyzer Capillary Electrophoresis system (Waters, Mildford, Mass., U.S.A) with a Millenium (Waters) software for data analysis. The sample was fed by hydrodinamic injection (10 cm height, over 20 seconds). The equipment has a silicon capilar 68 cm effective length and 50 um diameter, passed through by a small amount of sample (nl order). The protein migration occured from anode to cathode, a $H_3PO_4$ 150 mM solution (pH 1.5) was used as pulling electrolyte, allowing to keep the protein with a positive charge. The running time was 30 minutes. The electrophoretic analysis was made at 18 Kvolts and 25° C. Following electrophoresis, the capillary column was cleaned for 2 minutes with NaOH 0.5 M, followed by injection of distilled water for 2 minutes more. The detector used was UV. The working wavelength was 185 nm (peptidic bond absorption). The rationale for interpretation of capillary electrophoresis results (CE) was based on the Lambert-Beer Law (Harris, 2001), $A=k*C$, wherein A corresponds to detected absorbance, C is the sample concentration and k constant directly proportional to E, coefficient of absorptivity or molar extinction. Information is changed from absorbance to voltage difference (mV), such that area under the peak is proportional to $\epsilon*C$.

One-Dimensional, Agarose Gel Immunoelectrophoresis

The method described by Walker (1996) was used with minor modifications. An agarose 1% w/v (Type VII) solution was melted in buffer barbital 0.03 M, pH 8.4 and placed in a bath at 55° C. Later, about 4 mL of melted agarose was added to a slide, washed with ethanol, and left cooling for 5 minutes. Simultaneously, the chamber was filled with running buffer and slide-sized pieces of Whatman filter paper, which were later used to contact the gel with the barbital buffer. Next, a central channel of 1-mm wide well was made in the solidified agarose. This channel was filled with 3 ul of the antigen solution (around 15 ng) plus 1 drop bromophenol blue to follow up the protein migration. A potential difference of 600 V between cathode and anode was applied at 20 mA current for 1.5 to 2 hours, at 4° C. After electrophoresis, 100 ul anti-hemocyanin made in mouse serum was placed on the canal, available at the Biosonda's Research and Development laboratory, over 4 hours at room temperature. Gels were washed with PBS buffer and dried at a room temperature. Then, proteins were stained with the dyeing solution for agarose gels in immunoelectrophoresis (methanol 50%, acetic acid 10% and Amido Black 0.1%). The fading solution used was the same as one used for polyacrylamide gels.

E. Spectral Properties of Hemocyanins Through SERS (Surface Enhanced Raman Spectroscopy).

The study of hemocyanin structure by SERS was performed according to the procedure described by Leyton et al. (2205) with collaboration of Dr. Marcelo Campos, Spectroscopy Laboratory of the Universidad de Chile. Briefly, an hemocyanin aliquot (50 to 100 ug) was mixed with a silver ($Ag°$) colloidal solution prepared from $AgNO_3$ reduction by hydroxylamine ($NH_2OH$) in aqueous medium. The SERS spectrum of the colloidal solution was recorded through a RM1000 Renishaw Raman Microscope System equipment, provided with a light microscope, excitation laser (514 nm line), and a CCD detector. The working region at the electromagnetic spectrum covered from 4000 to 50/cm. The SERS spectrum was obtained by the use of a 50× lens (micro measurements). The output laser power was between 0.1 and 2.0 mW. The spectrum resolution was 4/cm. The recording conditions or scanning time were chosen to avoid denaturation of biological samples.

F. Copper Content

The copper content was determined by atomic absorption spectroscopy in a GBC equipment, model SENSAA, whose emission source is a hollow cathode lamp, emitting at 324.8 nm (Photon). The pre-treatment of purified FLH, FCH and FMH samples consisted of hydrolysis of organic matter with $HNO_3$ on an electric iron. Before the analysis, the solution obtained was diluted with HCl. A 1,000-ppm concentration, copper standard was used (Merck). This analysis was made at the Centro de Servicios Externos at the Facultad de Química of the Pontificia Universidad Católica de Chile.

Results

A. Extraction and Purification of Hemocyanins from Hemolymph of Three Chilean Limpet Species.

Characteristics of Limpet Species and Hemolymph

Figure 2:
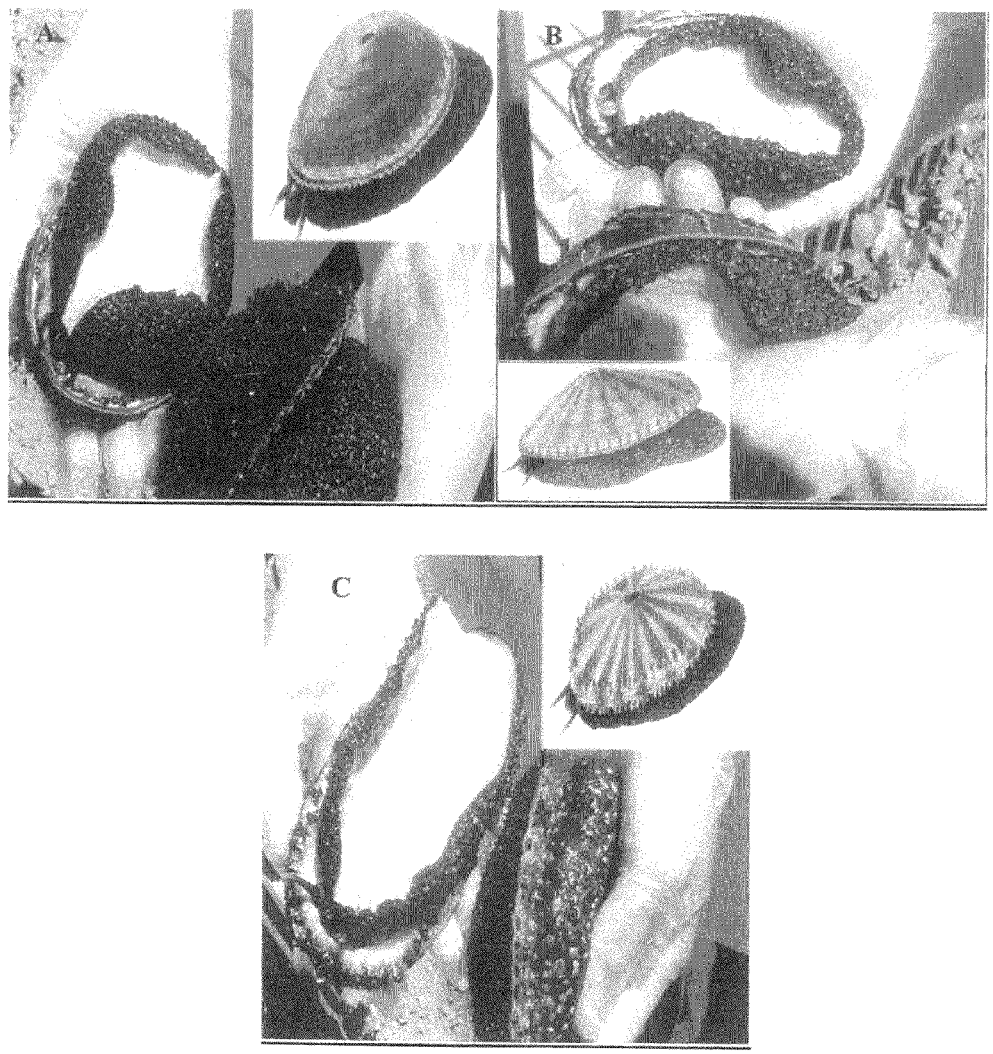
FIG. 2 figure shows the physical aspect of the three limpet species under study.

In Table I, physical parameters of adult species used for hemolymph extraction are shown, together with some of their characteristics, where the higher volume of hemolymph/animal in specimens of *Fissurella maxima* stands out. In FIG. 2, the three studied species are shown. It can be observed that *F. latimarginata* (FIG. 2A) has a black ventral foot and *F. cumingi* (FIG. 2B) has a pink foot, which give the common name to both species: Black limpet and strawberry limpet, respectively. In the case of *F. maxima* (FIG. 2C), the common name comes from the larger size of the animal, queen limpet. The extraction process through incision of the foot ventral area was fast and easy, taking 5 to 10 minutes by specimen and with care to under sterility conditions, to avoid endotoxin contamination for later use as antigen in order to assess immunogenicity in the humoral immune response of three mouse strains. The hemolymph had blue colour and homogeneous aspect.

TABLE 1

Some physical parameters of experimentation animals and its hemolymph

| Parameter | Species | | |
|---|---|---|---|
| | Fissurella latimarginata (Black limpet) | Fissurella cumingi (Strawberry limpet) | Fissurella maxima (Queen limpet) |
| Physical | | | |
| Size (cm) | 9.11 ± 0.72 | 9.18 ± 0.95 | 10.92 ± 0.77 |
| Weight (g) | 176.55 ± 29.61 | 166.85 ± 35.20 | 251.33 ± 46.21 |
| Hemolymph | | | |
| Volume total (ml) | 140 | 250 | 255 |
| Volume per animal (ml) | 12.7 | 19.2 | 28.3 |
| pH | 7.0-7.5 | 7.0-7.5 | 7.0-7.5 |

The recorded data correspond to eleven specimens of *F. latimarginata*, thirteen specimens of *F. cumingi* and nine specimens of *F. maxima*. The total volume per species was obtained through a hemolymph pool. The approximate volume per animal was determined dividing the total volume obtained for every species by the number of specimens used.

B. Precipitation of Hemocyanins and End Product of Dialysis

Figure 3:
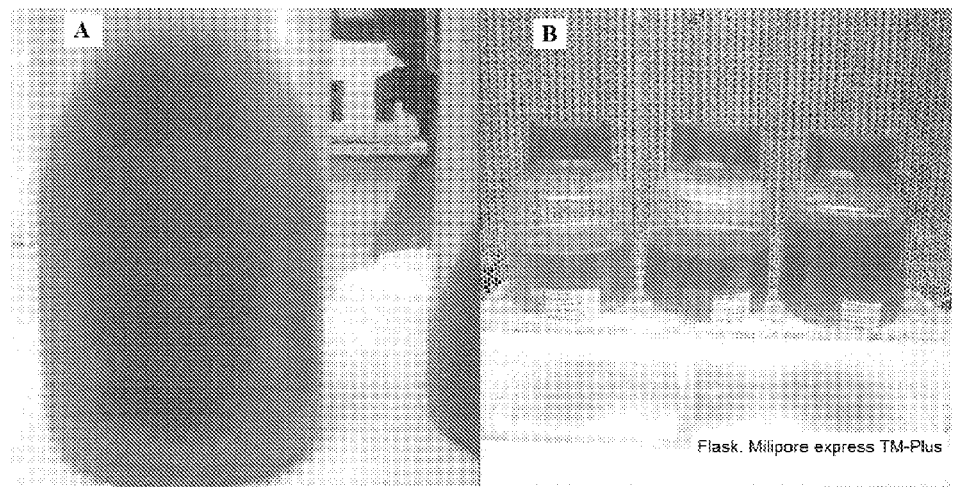
FIG. 3 shows the aspect of hemocyanin after precipitation process and dialysis.

Precipitation of hemocyanins from the hemolymph of experimentation animals was performed by slow and gentle stirring to avoid protein denaturation. FIG. 3A shows aspect of the precipitation end product using ammonium sulphate, and FIG. 3B shows the dialysis end product. From previous references related to hemocyanin of *Megathura crenulata*, KLH (Gebauer et al., 1994) and other species (Van Holde y Miller, 1995), maintenance of the quaternary structure in these proteins requires the presence of ions $Ca^{+2}$ and $Mg^{+2}$, due to which the precipitate was resuspended in the stabilizing buffer and dialized against it, with a goal to remove the ammonium salt and leave hemocyanin in an adequate solution. Both the precipitate (FIG. 3A) and purified protein (FIG. 3B) had the characteristic blue color of hemocyanin, where the color was more intense in this last preparation.

The hemolymph protein concentration was determined as per the Comassie blue method, using NaCl 0.9% w/v to prepare dilutions. Values measured were as follows: FLH, 6.91 mg/ml; FCH, 12.24 mg/ml and FMH, 10.25 mg/ml. The KLH concentration described in the Literature is 10 mg/ml (Gebauer et al., 1994), similar to that found in FMH. Similarly, the CCH concentration is around 15 mg/ml (De loannes et al., 2004), higher than found in the 3 study limpet species, under the same working conditions.

C. Biochemical Characterization of Limpet Hemocyanins

Structural Analysis Through Transmission Electronic Microscope

Figure 4:
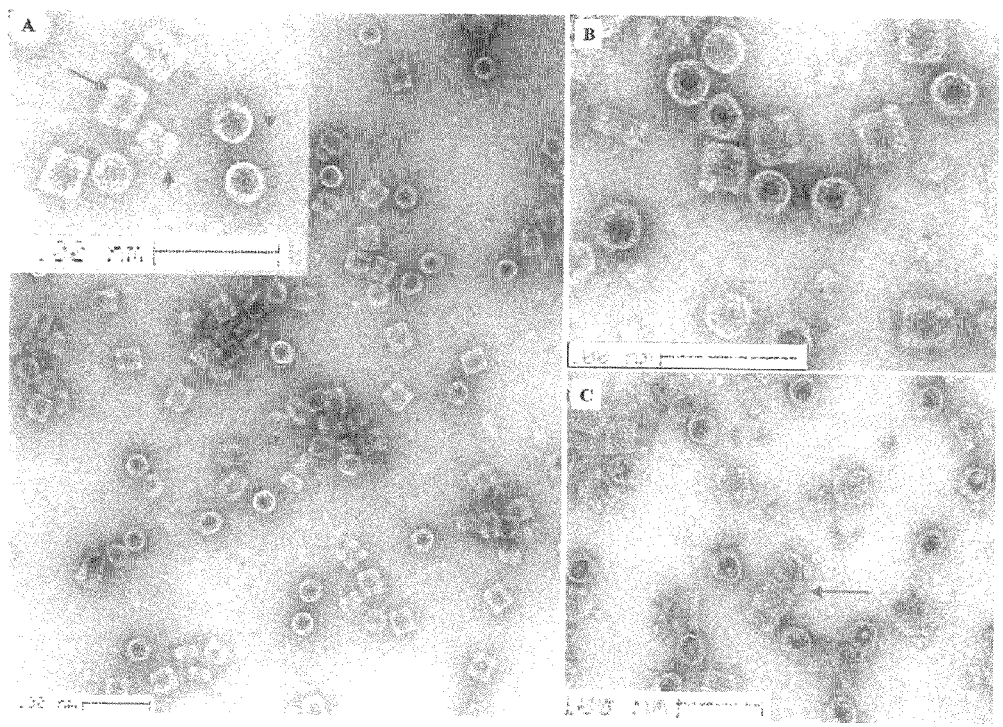
FIG. 4 shows the quaternary structure of hemocyanins from the three limpet species through negative dye on TEM.

Analysis of FLH, FCH and FMH samples through negative dye staning showed that the purification procedure yielded a homogeneous-sized protein solution. FIG. 4 shows TEM image aspect of hemocyanins from the 3 study limpet species. Hemocyanin from *Fissurella cumingi* (FIG. 4A), hemocyanin from *Fissurella latimarginata* (FIG. 4B) and hemocyanin from *Fissurella maxima* (FIG. 40). It was shown that organization of the hemocyanin quaternary structure of these gastropods mainly corresponds to didecamers. Just few decameric shapes were observed in the FCH solution and the presence of some multimers in FMH.

Table II summarizes sizes of hemocyanins of the three species under evaluation. Like hemocyanin of *Megathura crenulata* and *Concholepas concholepas*, their size is very large, within a similar range to KLH and CCH, despite the *Fissurella maxima* hemocyanin seems to be larger.

TABLE II

Estimated size of limpet hemocyanins*

| Species | Diameter (Å) | Height (Å) | Wide (Å) | Volume (Å$^3$) * 10$^6$ |
|---|---|---|---|---|
| 1. Experimental | | | | |
| F. latimarginata | 325 +/− 17.4 | 368 +/− 20.6 | 362 +/− 9.5 | 30.6 +/− 4.5 |
| F. cumingi | 339 +/− 13.1 | 380 +/− 11.6 | 350 +/− 5.3 | 34.3 +/− 3.2 |
| F. maxima | 363 +/− 13.1 | 387 +/− 14.4 | 380 +/− 11.7 | 40.3 +/− 2.9 |
| 2. References** | | | | |
| C. concholepas | 325 | 392 | 392 | 32.5 |
| M. crenulata | 310 | 345 | 345 | 26.0 |

*To estimate size, electron mycroscopy photograph obtained with negative staining were used. To determine diameter, from seven to fourteen hemocyanin molecules per species were measured, and between nine and fifteen molecules per species for length and wide. To obtain these values, three photos of hemocyanins per species were selected. Each photo was divided in six squares and diameter, height and wide of two proteins per square were determined, provided that the molecule quaternary structure was clearly stated. Then, the average of registered parameters was obtained for the three photos per species. Measurement was made by a mm-scaled magnifying glass.
**The *M. crenulata*'s hemocyanin size was determined from a molecule of an image published by Harris & Markl. (1999). The *C. concholepas*'s hemocyanin size was obtained from information published by De loannes et al. (1994).

D. Analysis of Polypeptide Composition Through Various Types of Electrophoresis

Figure 5:
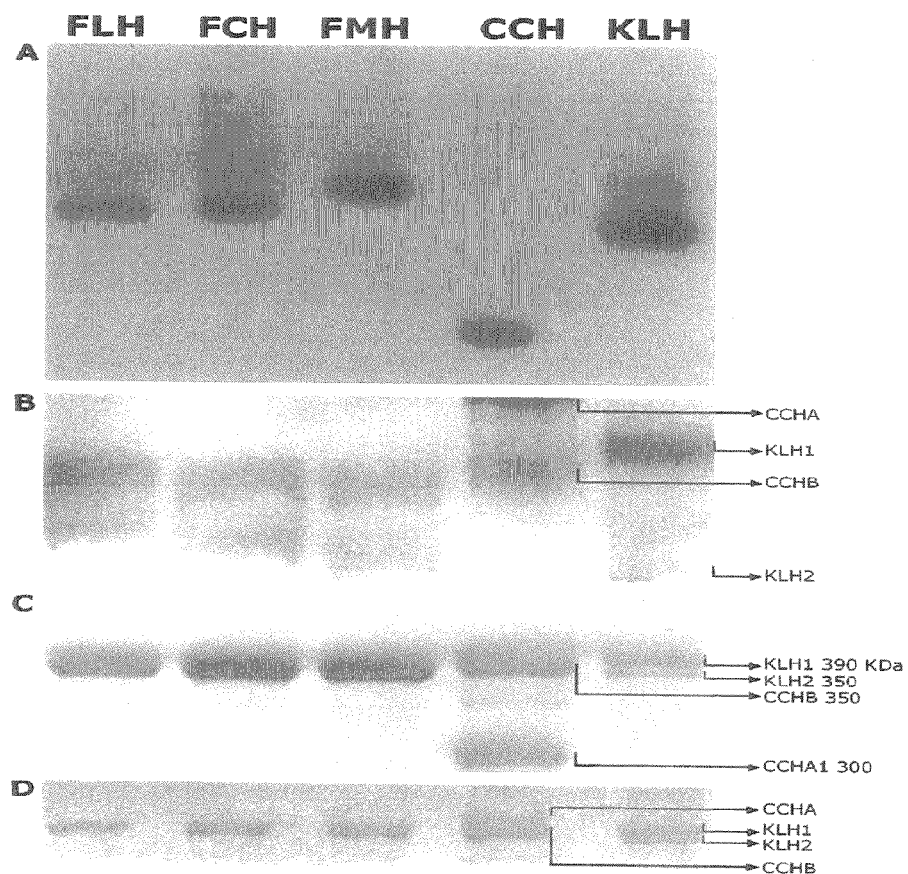
FIG. 5 shows the electrophoretic analysis of limpet hemocyanins.
Figure 6A:
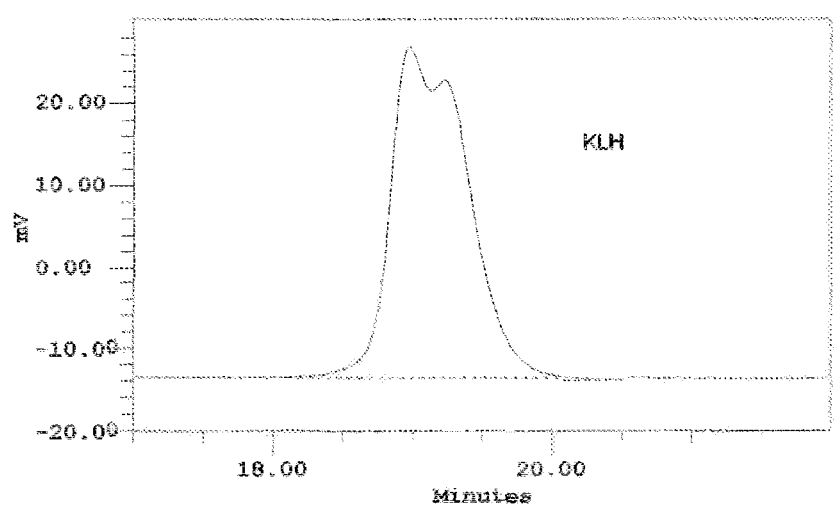
FIG. 6 shows chromatograms obtained from capillary electrophoresis of limpet hemocyanin samples. A sample around nl was injected and used as pulling electrolyte a solution of $H_3PO_4$ 150 mM (pH 1.5). The running time was 30 minutes. The electrophoretic analysis was performed at 18 volts at 25° C. The ordinate corresponds to the potential difference (mV) and the abscissa to run time (minutes).
Figure 6B:
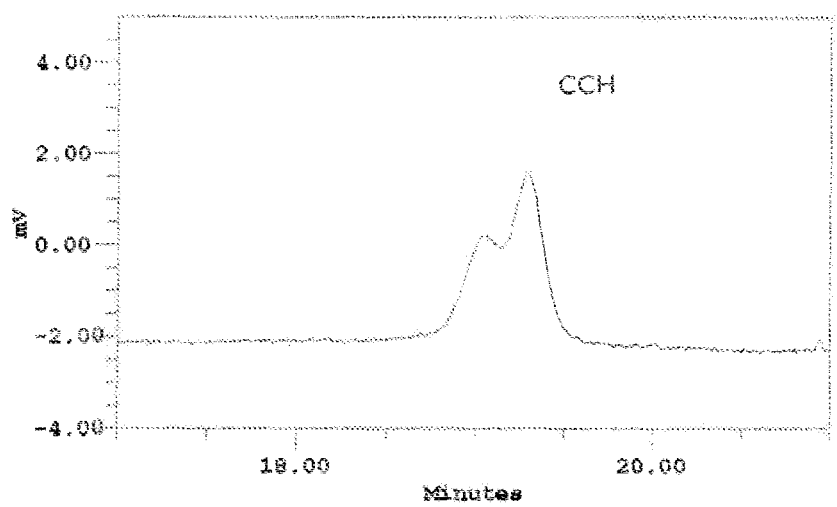
Figure 6C:
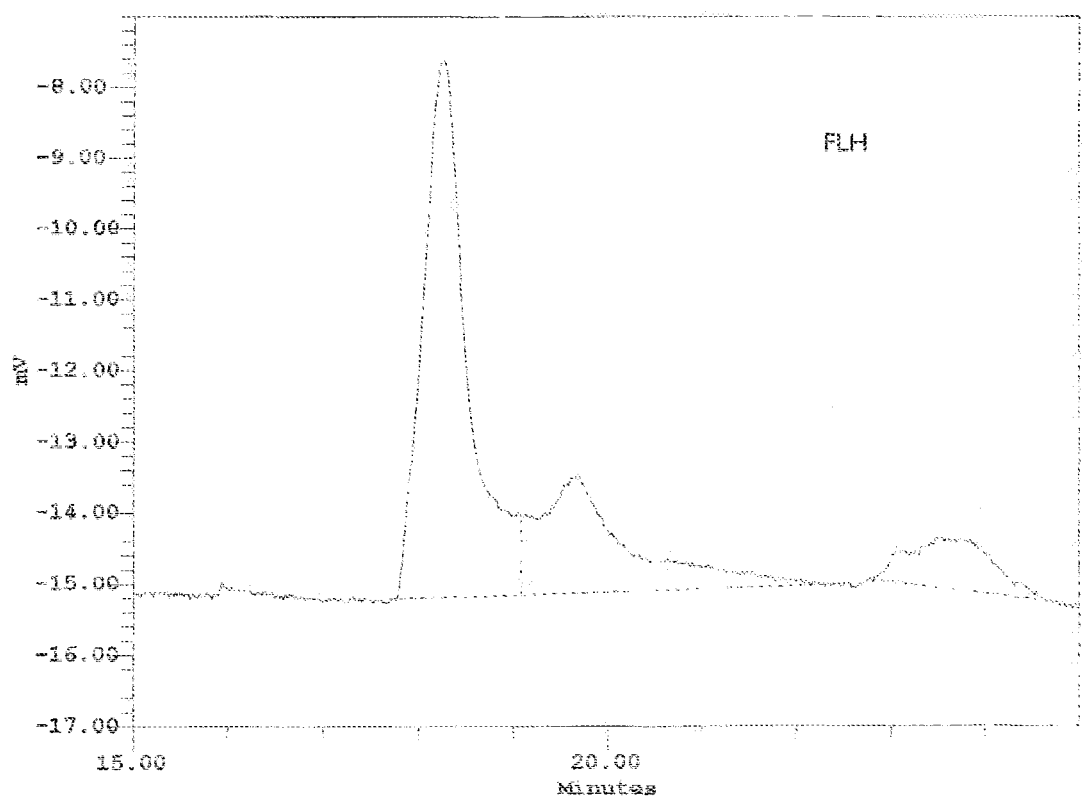
Figure 6D:
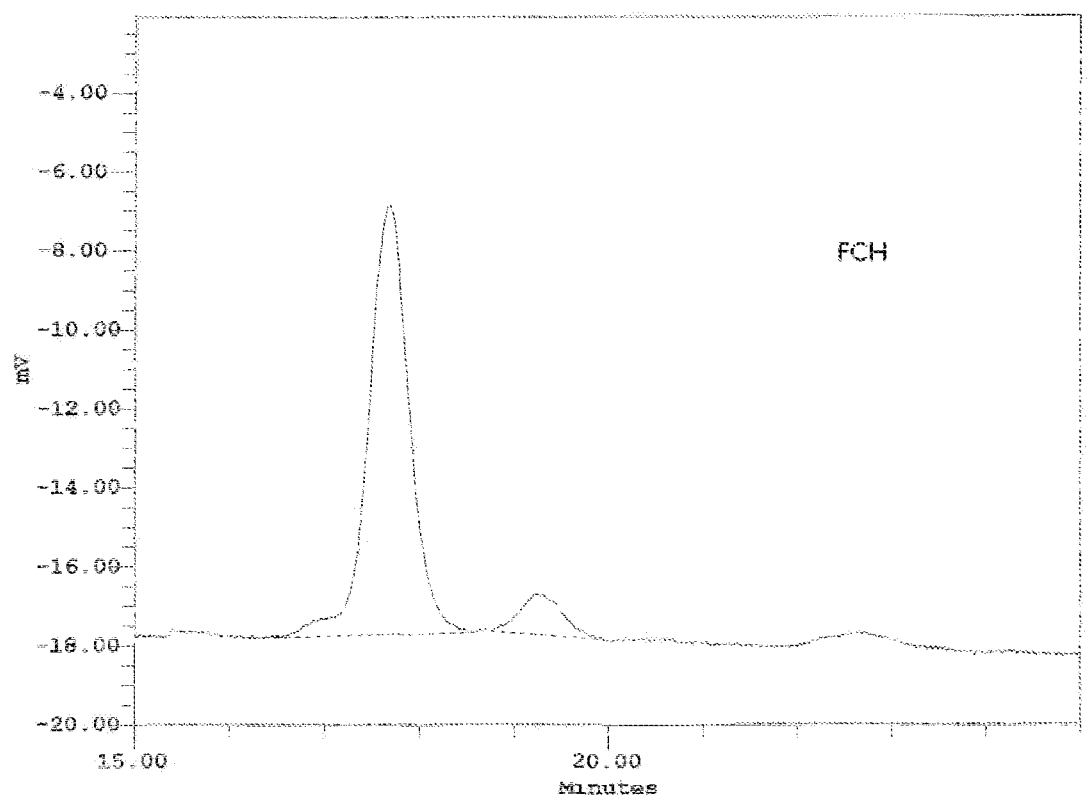
Figure 6E:
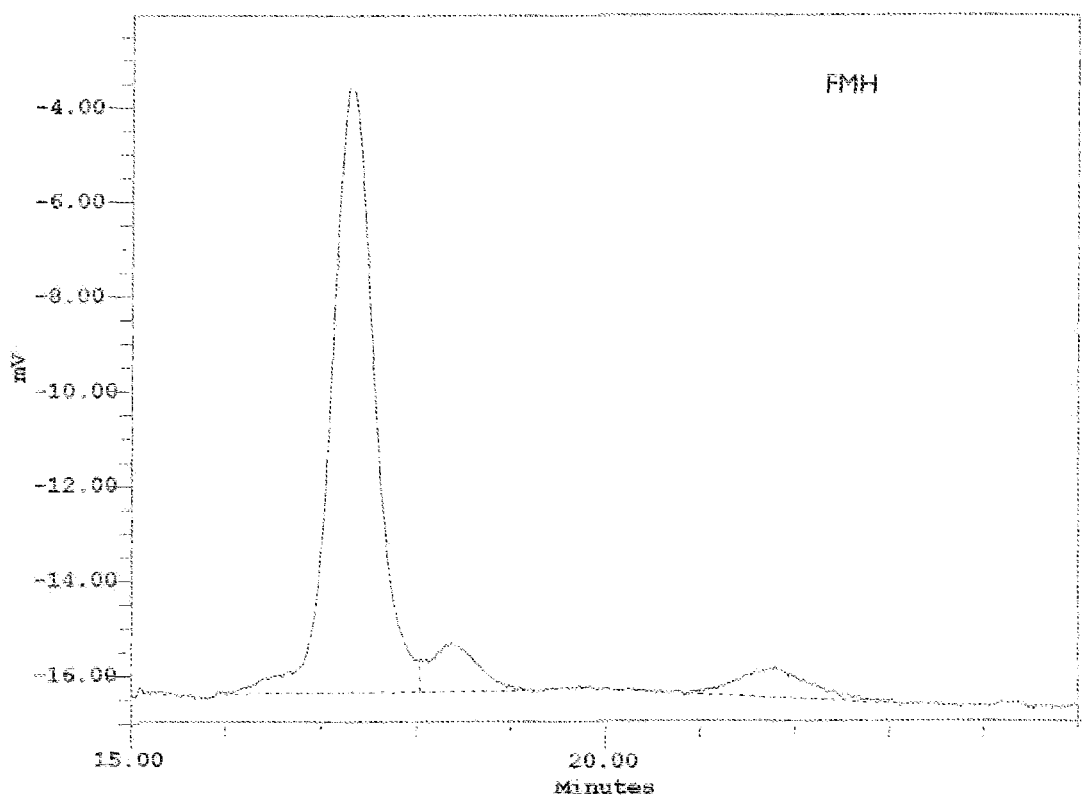

The polypeptide composition of hemocyanins, as purity criterion, was studied through different electrophoretic techniques. First, a native agarose gel electrophoresis was performed. Results from these electrophoretic experiments are shown in FIG. 5A, wherein the presence of a strongly stained band is observed for each one of the three studied hemocyanin samples. CCH and KLH were used as controls, which showed just one band.

FIG. 5B depicts polyacrylamide gel electrophoresis under native and dissociating conditions for hemocyanins, showing two types of polypeptides in the limpet hemocyanin samples, as well as for controls, CCH and KLH.

FIG. 5C depicts electrophoresis under reducing denaturating conditions, wherein migration per molecular weight of polypeptides present in the hemocyanin samples is recorded, after molecule denaturation and reduction of disulphur bonds required to maintain the protein tertiary structure.

Unlike what is observed in FIG. 5B, just one band is recorded in the gel for FLH, FCH and FMH. This finding suggested that both types of polypeptides present in the purified hemocyanin solution would have a similar relative molecular mass (Mr). The Mr obtained for subunits of study limpet hemocyanins was around 353 KDa, similar to observed for the subunit CCH-B of CCH (De Ioannes et al., 2004) and for the subunit KLH2 of KLH (Gebauer et al., 1994). The Mr obtained for CCH and KLH subunits was used as molecular weight standars.

FIG. 5D shows migration of polypeptides present in the purified hemocyanin samples under denaturating conditions, but in the absence of reducing agent. In the case of hemocyanins, FLH, FCH and FMH in study, just one band is observed, suggesting the lack of covalent bonds among comprising polypeptides. For hemocyanin present in the recently purified hemolymph of *C. concholepas*, CCH (control), the literature background is observed (De Ioannes et al., 2004), i.e., presence of two types of polypeptides comprising the molecule, CCH-A and CCH-B, which do not have covalent bonds between them, as well as in the other control, KLH, which does not even present disulphur bonds among subunits in every of the homodidecameric isoforms, KLH1 and KLH2, whose subunits are also referred as KLH1 and KLH2, respectively.

Capillary Eletrophoresis

FIG. 6 shows the EC results for the three limpet species, and KLH and CCH as control. Under working conditions, the technique was not resolutive, because, in the case of KLH and CCH, the total separation of both peaks related to both types of subunits described, KLH1 and KLH2 (Gebauer et al., 1994, Harris et al., 1995) and CCH-A and CCH-B (De Ioannes et al., 2004), respectively, was not obtained, but they are suggested. In the case of limpets, the presence of a main peak was observed, followed by a smaller one.

One-Dimension Immunoelectrophoresis

Figure 7:
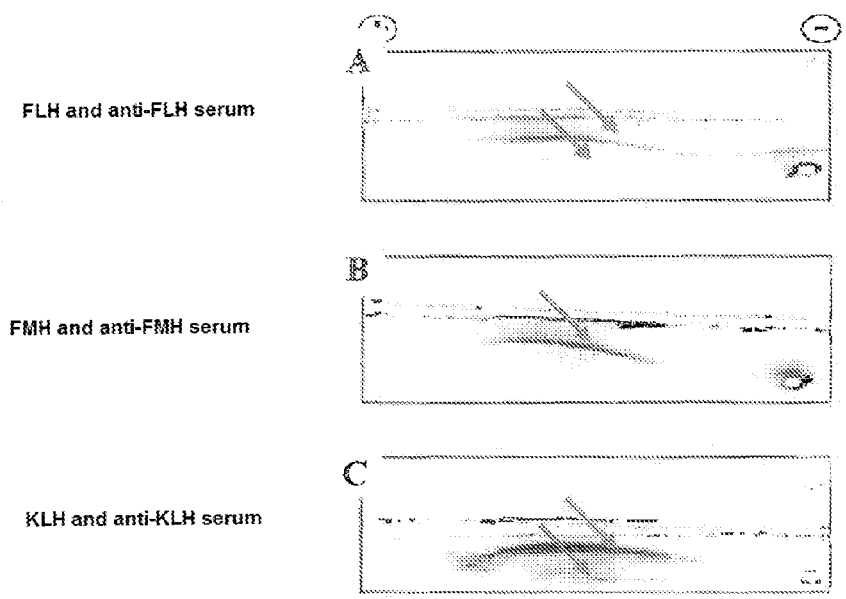
FIG. 7 shows one-dimensional agarose gel immunoelectrophoresis where

FIG. 7 shows the agarose gel immunoelectrophoresis results for the FLH and FMH samples, and KLH as control. FIG. 7A shows precipitation reaction beteween the FLH sample and its antiserum; two precipitation arcs are observed, suggesting the presence of two isoforms in the hemolymph of *F. latimarginata*, a result different from one observed for the reaction between the FMH sample and its antiserum (FIG. 7B), showing just one arc, suggesting the presence of one molecule in the hemolymph of *F. maxima*. FIG. 7C shows results for the KLH sample, depicting two precipitation arcs due to two protein isoforms in the hemolymph of *M. crenulata*. No results were obtained for the FCH sample due to lack of antiserum.

E. Spectral Properties of Hemocyanins Through SERS

FLH Analysis

Figure 8:
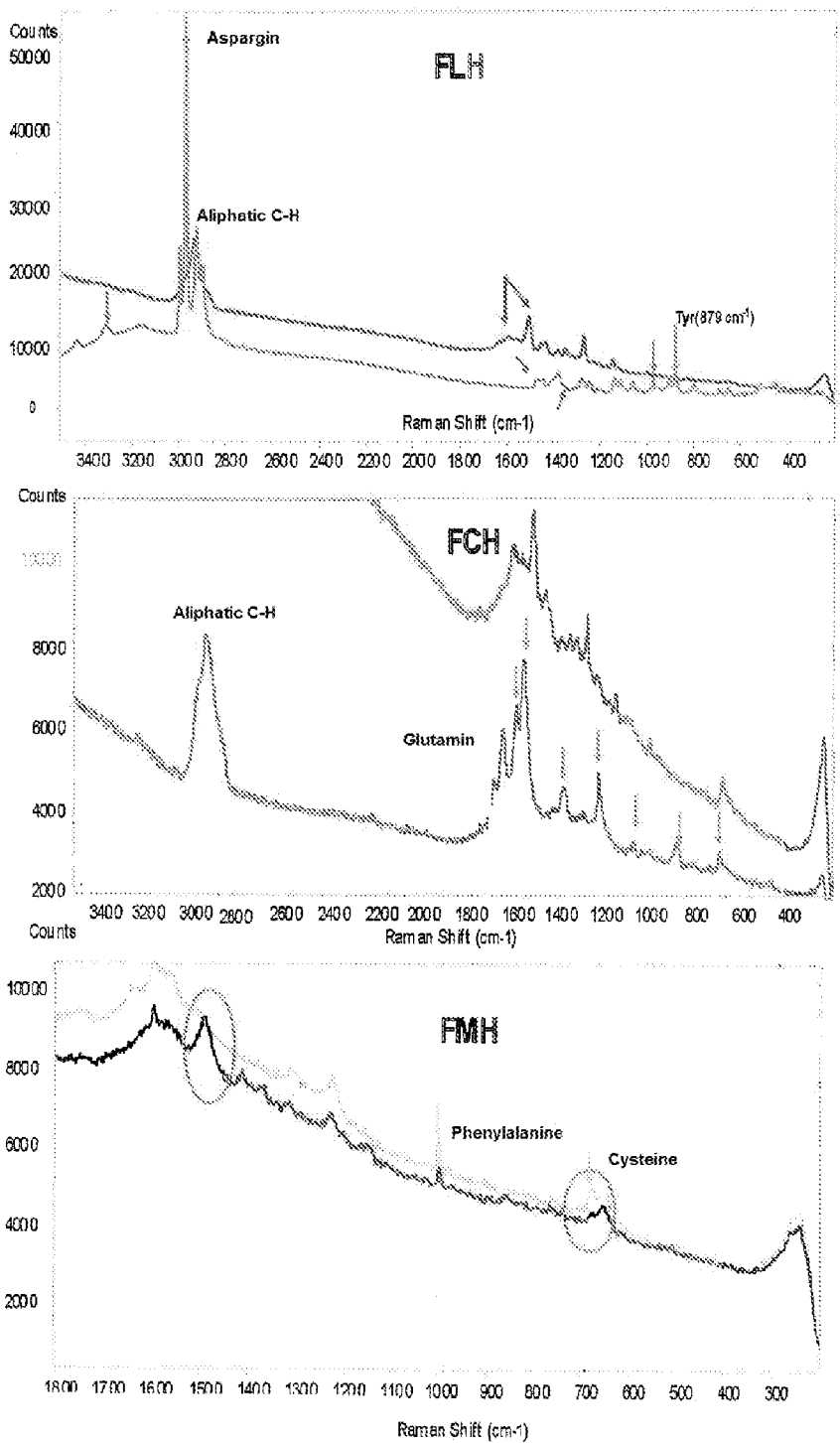
FIG. 8 shows the SERS spectrum for the hemocyanin colloidal solutions of the study. After purification, an hemocyanin sample (50 and 100 ug) for every study species was suspended on a metallic silver colloidal solution for spectroscopic SERS analysis. Working conditions were as follows: Excitation laser, 514 nm; laser incidence area, 1 $um^2$; number of measurements, 50 to 100/spectrum; a Renishaw Raman Microscope System equipment was used. Each vibrational spectrum recorded is related to spectroscopic characteristics typical of aminoacid functional groups, present on the surface of every hemocyanin molecule. In the FLH spectra, the red arrows over a spectrum correspond to vibrations typical of functional groups of asparagin residues, absent in the other spectrum of the figure. In the FCH spectra, the green arrows over a spectrum correspond to vibrations typical of functional groups of glutamine residues, absent in the other spectrum of the figure. Differences among the FMH spectra are indicated as red circles.

FIG. 8A shows two different SERS spectra for the same FLH sample in red and blue. Both red and blue SERS spectra show clear and isolated bands in the area covering from 1,700 $cm^{-1}$ to 400 $cm^{-1}$. Clear differences between both spectra can be registered in the area around 3,000 $cm^{-1}$. In the red spectrum, bands at 3,307 $cm^{-1}$, 2,990 $cm^{-1}$ and 2,968 $cm^{-1}$ were observed, together with bands at 1,473 $cm^{-1}$, 1,356 $cm^{-1}$ and 980 $cm^{-1}$, proper of the aminoacid asparagin (Asn). A band of 879 $cm^{-1}$ corresponding to thyrosine (Tyr) was also recorded, similar to observed by Leyton et al. (2005), in KLH. Common bands for both spectra are also observed, such as 1,451 $cm^{-1}$, 1,381 $cm^{-1}$, 1,267 $cm^{-1}$ and 1,145 $cm^{-1}$, which would correspond to the same aminoacids in both types of hemocyanins (because they arise at the same frequency), but with other arrangement (because of a different band intensity). The blue spectrum showed just one peak around 3,000 $cm^{-1}$, corresponding to vibrations in the C—H aliphatic-type bond. It also showed bands at 1,592 $cm^{-1}$ and 1,500 $cm^{-1}$, not observed in the red spectrum, suggesting both proteins are different.

FCH Analysis

Similarly to FLH, the FCH sample gave two types of SERS spectra (FIG. 8B). In both green and pink spectra, clear and isolated bands were observed in the region covering from 1,700 $cm^{-1}$ to 400 $cm^{-1}$ and a peak around 3000 $cm^{-1}$, corresponding to vibrations in the C—H-type bond (not shown in the pink spectrum). The pink spectrum was identical to that described for one of the two molecular groups present in the hemolymph of *Fissurella latimarginata* (blue spectrum.).

In the green spectrum, bands at 2,927 $cm^{-1}$ were recorded (coresponding to vibrations in the C—H-type bond), 1,670 $cm^{-1}$, 1,640 $cm^{-1}$, 1,573 $cm^{-}$and 1,540 $cm^{-1}$, along with bands at 1,367 $cm^{-1}$, 1,215 $cm^{-1}$, 1,060 $cm^{-1}$, 880 $cm^{-1}$ and 688 $cm^{-1}$ plus a band at 245 $cm^{-1}$, similar to the spectrum for the aminoacid gluthamine (Gln). These bands were not recorded in the pink spectrum, suggesting both proteins are different.

FMH Analysis

For the FMH sample, two types of SERS spectra were observed, which, unlike observed in the FLH solution (FIG. 8A), differ on the presence or absence of some bands in the region 1,800-400 $cm^{-1}$ (FIG. 8C). In the black spectrum, a well defined band is seen at 1,491 $cm^{-1}$, absent in the orange spectrum. Besides the above-mentioned, in the region between 700 $cm^{-1}$ and 600 $cm^{-1}$, the orange spectrum presented at least two bands attributable to the amino acid cysteine (Cys), according to the studies by Leyton et al. (2005) on KLH.

Copper Content

The copper content found in a FLH and FCH solution was 0.16% w/w, corresponding to a molar ratio of 174 copper moles/mol intact protein. For the FMH solution, a value of 0.14% w/w was obtained, equivalent to a molar ratio of 149 copper moles/mol intact protein.

Example 2

Immunogenic Characterization of Purified Limpet Hemocyanins

Methods

A. Assessment of Mouse Anti-Hemocyanin Sera

Mouse Immunization and Serum Collection

Step 1: Fifteen animals per strain were used in total (around three-month age), being separated in groups of three animals for each antigen in study (FLH, FCH, FMH) and for controls (CCH and KLH). Identification was made through mouse ear cuts. Before immunization, a blood sample was taken from the tail of all the animals, to obtain the pre-immune serum as control.

Animals were immunized intraperitoneally by 200 ug/animal of an hemocyanin solution in stabilizing buffer. After 14 days, a new blood sample was drawn from immunized animals, in order to assess the primary humoral immune response. To collect sera, the blood sample was centrifugated at 12,000 rpm for 5 min and then stored at −20° C. until use. The following day, animals received 200 ug antigen/animal and, 14 days after, a new blood sample was drawn, corresponding to the secondary humoral immune response.

Step 2: As a way of confirming the results obtained, the experiment was once repeated, but only in BALB/c strain mice. Unlike the methodology developed for the first step animals, a third immunization with the antigen was performed (1 mg/animal) to obtain a hyperimmune serum. This serum was used to develop one-dimension immunoelectrophoresis.

B. Assessment of the Humoral Immune Response of Mice Against Hemocyanins Through Antibody Titer Measurement by the ELISA Technique.

The general procedure used was the described by Crowther & Abu-Elzeein (1980), with modifications. Reacti-Bind™ plates were activated overnight at 4° C. with 100 ul/well of an antigen solution (FLH, FCH, FMH, CCH and KLH) at a concentration of 10 ug/ml in PBS buffer. Later, the plate solution was removed and the available plate sites were blocked with 100 ul/sump of PBS-casein (NaCl 0.15 M, sodium phosphate 0.1 M, casein 1% w/v) for 1 hour at room temperature. The plate solution was then removed and incubated with the first antibody (serum specific) for 1.5 hours at 37° C. Serum dilutions were made in PBS-casein and were as follows: 1:20, 1:40, 1:80, 1:160, 1:320, 1:640, 1:1,280, 1:2,560, 1:5,120, 1:10,240, 1:20,480 and 1:40,960, which in base 2 log is approximately equivalent to 4, 5, 6, 7, 8, 9, 10, 11, 12, 13, 14 and 15 dilutions. Next, the plates were wased three times(ELISA washer, 200 ul/wll with PBS-Tween 0.02% v/v). 100 ul/well of mouse anti-IgG (H+L) was added, developed in goat, conjugated with Alcaline Phosphatase (ALP), diluted 1/2,500 in PBS-casein and incubated for 1 hour at 37° C. Three washings of 200 ul/sump were made with PBS-Tween 0.02% v/v and then the plate was revealed. For this, 100 ul/well of solution 1 mg/ml pNPP was placed in plating buffer for ELISA and left incubating over 30 min at 37° C. The reaction was stopped with 100 ul/sump of NaOH 3N. The absorption value reading (DO) was performed at 405 nm, in a plate reader for ELISA. The cutt-off is 0.1 absorbance units. The technique error is +/−one dilution.

The seric antibody titer of each animal was defined as the serum dilution in which half of the maximum DO was obtained.

C. Determination of Anti-Hemocyanin Serum Specificity and Identification of Subunits Involved in the Crossed Reaction Through Western Blot, in BALB/c Strain Mice.

The general procedure described by Towbin & cols. was made (1979). Briefly, 2.5 ug/line of denaturated FLH, FCH, FMH, CCH and KLH samples were previously separated through gradient polyacrylamide gel electroforesis (separating gel 3 to 12% and concentrating gel 4%), under denaturating and reducing conditions (SDS-PAGE, β-mercaptoethanol). Later, gel proteins were transfered to a nitrocellulose membrane with pore diameter of 0.45 um, overnight at 50 mA and room temperature. For the transfer, a transfer buffer for Western blot was used (Tris 25 mM, glycine 192 mM and methanol 20% v/v).

Later, each membrane was left blocking at room temperature with PBS-casein buffer over 6 hours, with stirring and then incubated with sera on 1/200 dilution (in PBS casein buffer). Incubation was carried out overnight with stirring at room temperature. Later, three washings were made with PBS-Tween 0.02% v/v buffer, for 5 minutes each, with stirring at room temperature. Next, the conjugate was added (anti mouse-IgG ALP conjugated developed in goat) diluted 1/5,000 in PBS-casein buffer. Again, three washings were made with PBS-Tween 0.02% v/v buffer, for 5 minutes each, with stirring at room temperature. Finally, the revealing solution 1-Step™ NBT/BCIP was added for 5 to 10 minutes; the reaction was stopping by consecutive washings with milli-Q water.

Results

Immunogenic Characterization of Limpet Hemocyanins

Figure 9:
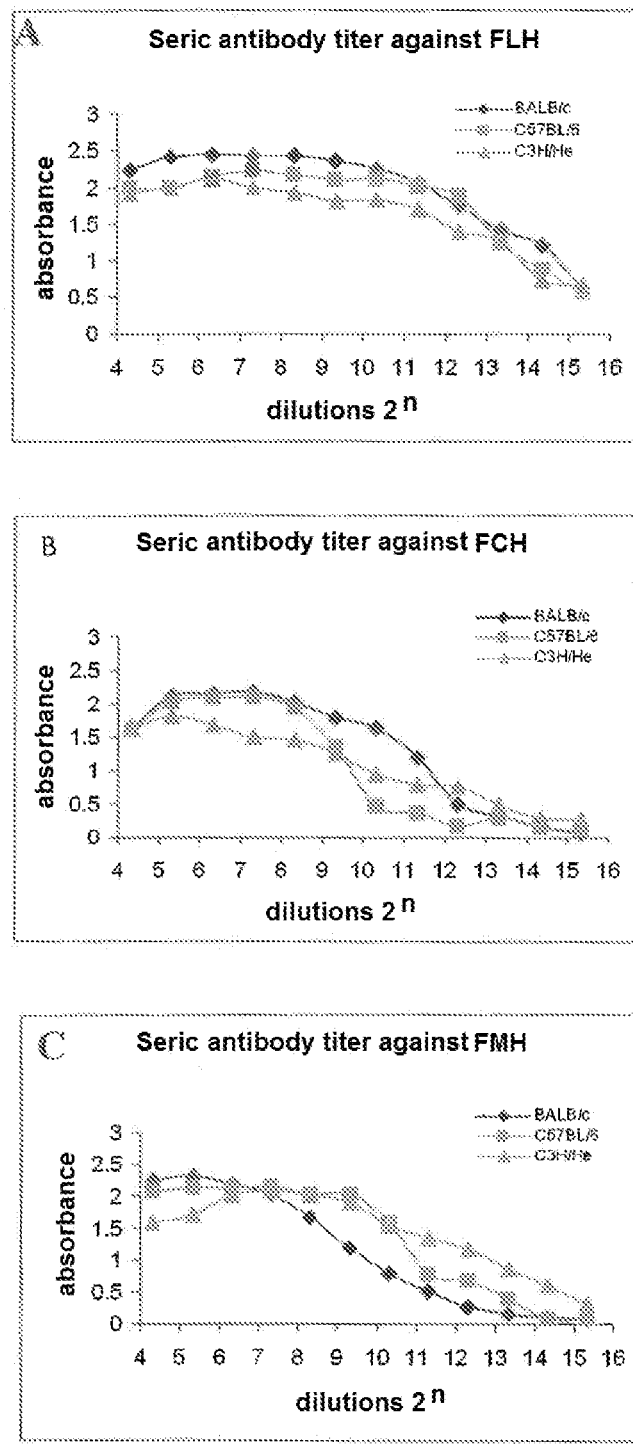
FIG. 9 shows the anti-hemocyanin secondary humoral immune response in three mouse strains, ussing a direct ELISA assay. Each experiment includes three mice per strain on average, with a difference among them below 10%.
Figure 9:
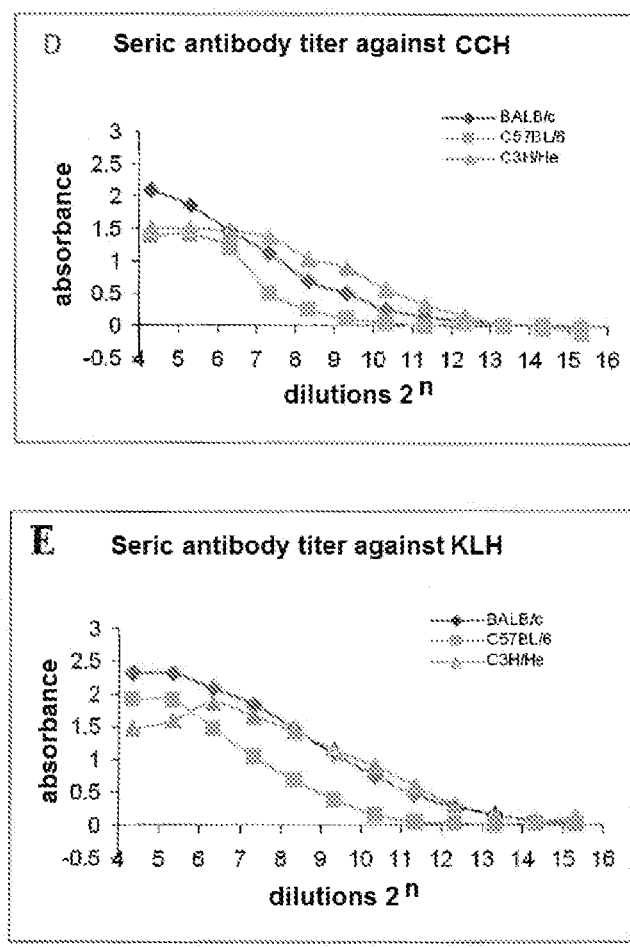

A. Study of Humoral Immune Response in Mice Immunized by Limpet Hemocyanins Through ELISA Assessment of the Primary and Secondary Immune Response Through direct ELISA, the seric antibody titer was determined with its homologous antigen, i.e., hemocyanin used to immunize mice from the three strains most used in immunology was placed on the plate. Mice immunized with CCH and KLH were used in parallel as controls. It should be noted that these assessments did not use additional adjuvants, therefore, the response is due to hemocyanins only. The seric antibody titer was defined as the dilution in which half of the maximum DO is obtained. Results of this experiment showed that the primary response (data not shown) developed in animals from the three different mouse strains, was clearly lower than the secondary response against the same antigen (FIG. 9 and summarized in Table III), being significant differences observed at immunization of animals with FLH (FIG. 9A), with titers being around 14 dilutions in the BALB/c strain, 13 dilutions in the C57B1J6 strain and 13 dilutions in the C3H/He strain. In case of FCH (FIG. 9B), the seric antibody titer was 11, 9 and 10 dilutions, respectively. For FMH (FIG. 9C), titers were found around 9, 11 and 12 dilutions, respectively. The secondary response induced in animals by CCH (FIG. 9D) and KLH (FIG. 9E) was markedly lower than FLH. For CCH, titers were found around 7, 7 and 9 dilutions, respectively, and for KLH, these were around 9, 7 and 10 dilutions, respectively.

Assessment of Crossed Reaction of Antisera Against Hemocyanins from Different Species, Through Direct ELISA.

Figure 10:
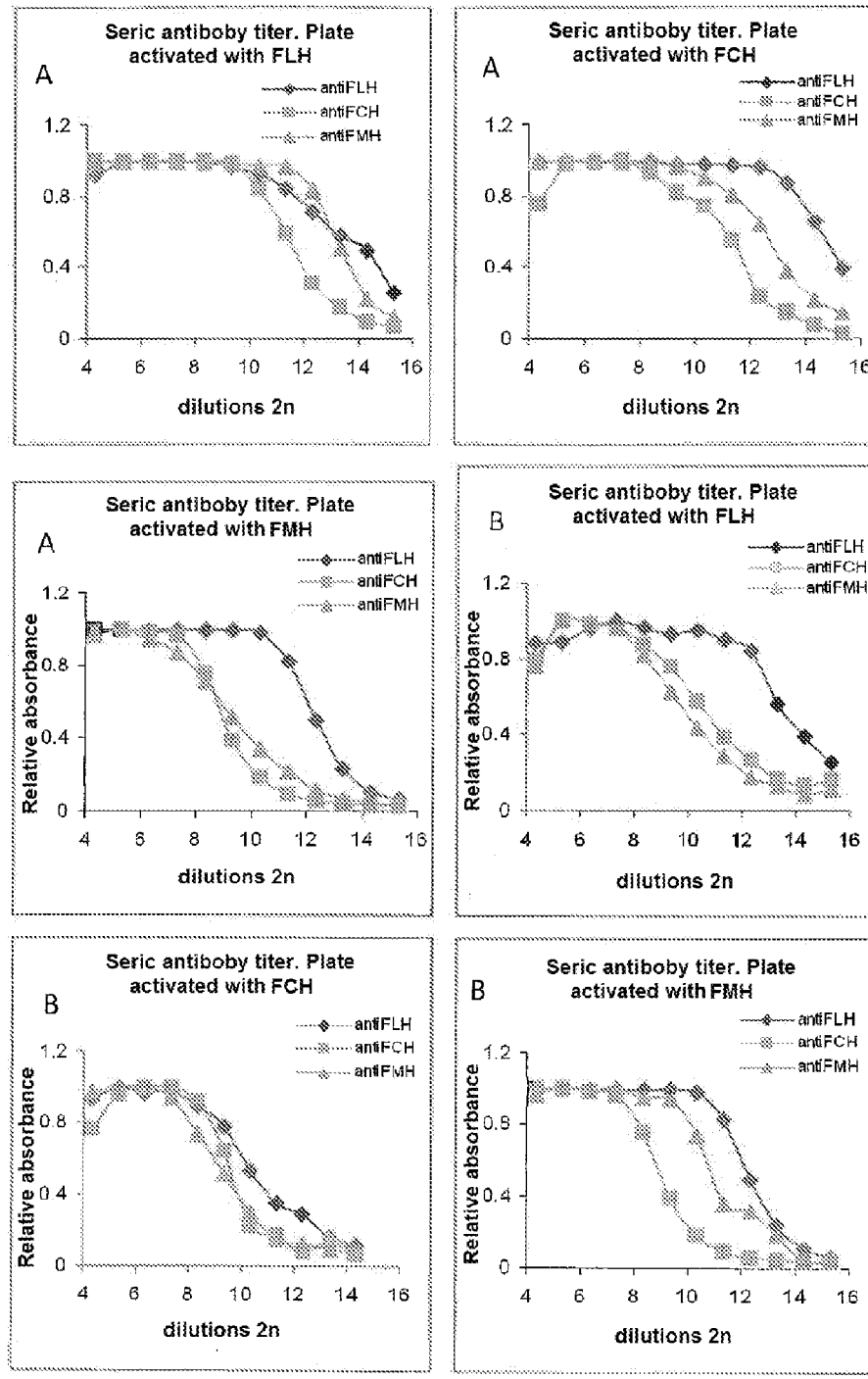
FIG. 10 shows the cross reaction of the anti-hemocyanin antisera in mice from different strains. Each graph represents the result of a serum pool from three mice of each strain.
Figure 10:
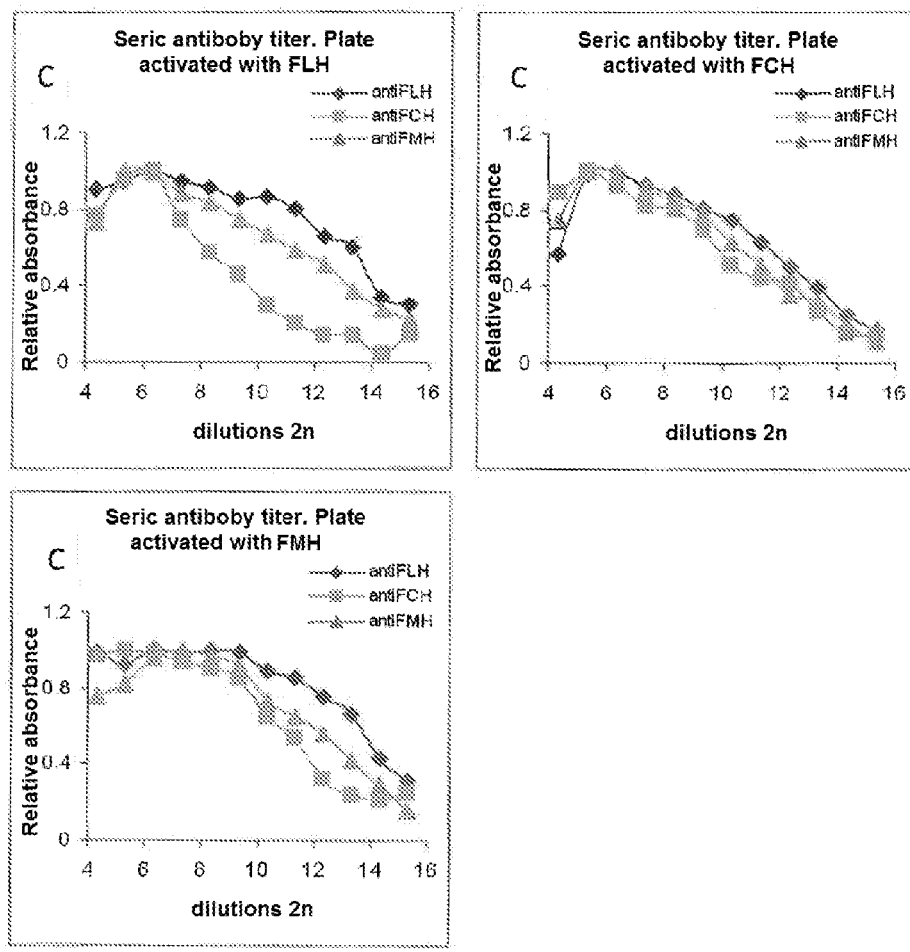

FIG. 10 shows the crossed reaction of antihemocyanin antisera against the non-homologous hemocyanins remaining and used as experimental antigens. The seric antibody titer was defined as above. In general terms, the crossed reaction among hemocyanins from the same family, FLH, FCH y FMH, is similar; however, an equal or higher titer is observed between FCH and FMH and the anti FLH serum than its homologous, in the 3 study strains (Table III). Because of the low crossed reaction between these antigens and KLH and CCH, comparisons with other hemocyanins were not performed.

TABLE III

Seric antibody titer with homologous and heterologous antigen, in three mouse strains

| Antigens* Strain** | Antiserum | FLH | FCH | FMH |
|---|---|---|---|---|
| | anti FLH | 14 | 14 | 12 |
| | anti FCH | 11 | 11 | 9 |
| BALB/c | anti FMH | 13 | 13 | 9 |
| | anti CCH | 5 | 5 | 4 |
| | anti KLH | 6 | 5 | 4 |
| C57BL/6 | anti FLH | 13 | 10 | 12 |
| | anti FCH | 10 | 9 | 9 |
| | anti FMH | 10 | 9 | 11 |
| | anti CCH | 5 | 5 | 5 |
| | anti KLH | 3 | 5 | 5 |
| C3H/He | anti FLH | 13 | 12 | 14 |
| | anti FCH | 9 | 10 | 11 |
| | anti FMH | 12 | 11 | 12 |
| | anti CCH | 5 | 4 | 4 |
| | anti KLH | 5 | 4 | 4 |

The seric antibody titer with homologous antigen stands out in bold, and normal letter for the crossed reaction of antisera of the three immunized strains with the heterologous antigen.
*For the CCH and KLH antigens, the titer could not be determined due to its low crossed reaction.
**The haplotypes of strains are: d for BALB/c, b for C57B/6 and k for C3H/He.

Assessment of Homologous and Heterologous Reactivity of Hemocyanin Antisera by Western Blot These experiments were only performed with antisera from BALB/c strain mice. When a membrane was incubated with an anti-FLH serum (FIG. 11B), three bands were clearly observed, corresponding to tracks wherein the denatured FLH, FCH and FMH samples were loaded, respectively, suggesting the subunits FCH and FMH share epitopes with FLH. It should be noted that intensity of these last two bands is similar to that of FLH subunits with their corresponding homologous antiserum (first lane).

When a membrane was incubated with an anti-FCH serum (FIG. 11C), a light and diffuse reactivity with FCH and FLH was observed. In contrast, in FMH, a clear and more intense band is observed, suggesting the reaction of FMH subunits with the anti-FCH serum is higher, even with FCH subunits.

When a membrane was incubated with anti-FMH serum (FIG. 11E), three intense bands with FLH, FCH and FMH were observed, respectively.

Figure 11:
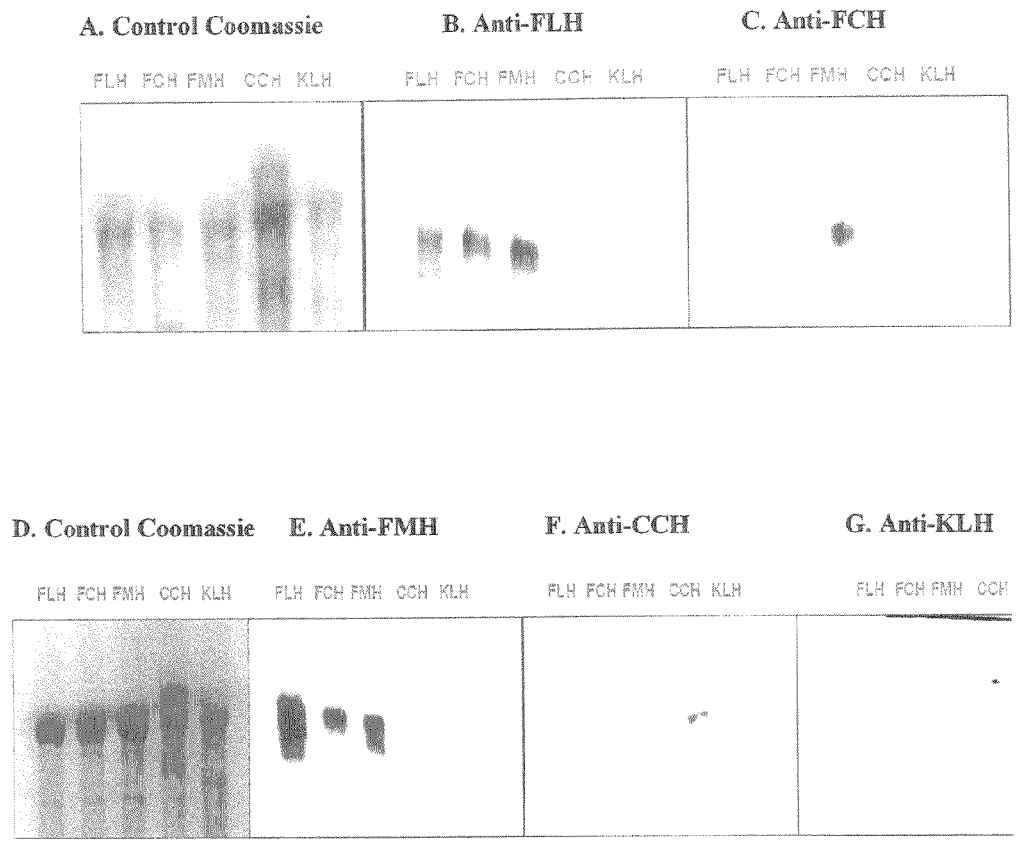
FIG. 11 shows shows the cross reaction among hemocyanins in animals from BALB/c strain by Western blot.

In the three previous figures, it was observed that there was no cross reaction among antisera of the three study limpet species and CCH and KLH subunits, supported by information disclosed in FIG. 11F, wherein reaction was recorded only between CCH subunits and the homologous antiserum. However, in FIG. 11G (membranes incubated with anti-KLH serum), a light and diffuse reactivity with FMH was observed, suggesting these hemocyanins share some epitopes. As expected, results from FIG. 11G showed a band in the rail where the KLH sample was loaded with the anti KLH antiserum.

In addition, a low-intensity band was observed in the lane where the CCH sample was loaded, suggesting both hemocyanins share some epitopes, according to the previous report (Oliva, 2002).

References

De Ioannes, P., Moltedo, B., Oliva, H., Pacheco, R., Faunes, F., De Ioannes, A. E. y Becker, M. I. (2004). Hemocyanin of the molluscan *Concholepas concholepas* exhibits an unusual heterodecameric array of subunits. J. Biol. Chem. 279, 26134-42.

Fernández-Morán, H., Van Bruggen E. y Ohtsuki, M. (1966). Macromolecular organization of hemocyanins and apohemocyanins as revealed by electron microscopy. J. Mol. Biol. 16, 191207.

Gebauer, W., Harris, R., Heid, H., Süling, M., Hillenbrand, R., Sdhngen, S., Wegener-Strake, A. y Markl, J. (1994). Quaternary structure, subunits and domain patterns of two discrete forms of keyhole limpet hemocyanin: KLH1 and KLH2. Zoology 98, 51-68.

Harris, R., Gebauer, W., Sóhngen, S. y Markl, J. (1995). Keyhole limpet hemocyanin (KLH): Purification of Intact KLH1 through selective dissociation of KLH2.Micron 26, 201-12.

Laemmli, U. K. (1970). Cleavage of structural proteins during the assembly of the head of bacteriophage T4. Nature 227: 680-685.

Leyton, P., Lizama-Vergara, P., Campos-Vallette, M., Becker, M. 1., Clavijo, E., Córdova, I., Vera, M. y Jerez, C. (2005). Surface enhanced Raman spectrum of nanometric molecular systems. J. Chil. Chem. Soc. 50, 725-30.

Oliva, H., Moltedo, B., De Ioannes, P., Faunes, F., De Ioannes, A. E. y Becker, M. I. (2002). Monoclonal antibodies to molluskan hemocyanin from *Concholepas concholepas* demonstrate common and specific epitopes among subunits. Hybridoma Hybridom. 21, 365-74.

Swerdlow R. D., Ebert R. F., Bonaventura C. y Miller K. I. (1996). Keyhole limpet hemocyanin: Structural and functional characterization of two different subunits and multimers. Comp. Biochem. Physiol. Biochem. Mol. Biol. 113: 537-548.

Towbin, H., Theophil S. y Gordon, J. (1979). Electrophoretic transfer of proteins from polyacrylamide gels to nitrocellulose sheets: Procedure and some applications. Biochemistry 76, 4350-4354.

Van Holde, K. E. y Miller, K. I. (1995). Hemocyanins. Adv. Protein Chem. 47,1-81.

Walker, J. M. (1996). The protein protocols handbook. Human Press., pp. 763.

The invention claimed is:

1. A purified hemocyanin, subunits or immunogenic fragments thereof, wherein the hemocyanin is purified from a hemolymph of *Fissurella latimarginata*(black limpet).

2. The hemocyanin according to claim I, wherein the hemocyanin purified from *Fissurella latimarginata* comprises didecamers comprising one type of subunit and having a diameter of about 325 Å, height of about 268 Å, and width of about 362 Å.

3. The hemocyanin according to claim I, wherein the hemocyanin purified from *Fissurella latimarginata* (black limpet) comprises an immunogenicity higher than the immunogenicity of hemocyanins purified from other gastropods.

4. A hemocyanin subunit purified from *Fissurella latimarginata* according to claim I, wherein the subunit has a relative molecular mass of about 353 KDa and a characteristic SERS Raman profile.

5. A composition comprising a purified hemocyanin, or subunits or immunogenic fragments thereof, in an amount sufficient to provide an immunostimulant or immunomodulator activity in a patient, wherein the hemocyanin is purified from a hemolymph of *Fissurella latimarginata* (black limpet).

6. The composition according to claim 5, further comprising a vehicle suitable for administration to the patient.

7. The composition according to claim 5, wherein the composition comprises from about 1 to about 500 mg/mL of hemocyanin.

8. The composition according to claim 5, wherein the composition comprises from about 5 to about 30 mg/mL of hemocyanin.

9. A method for inducing an immune response in a patient comprising administering a composition comprising a purified hemocyanin, or subunits or immunogenic fragments thereof, in an amount sufficient to provide an effective adjuvant effect, wherein the hemocyanin is purified from a hemolymph of *Fissurella latimarginata* (black limpet).

* * * * *

UNITED STATES PATENT AND TRADEMARK OFFICE
CERTIFICATE OF CORRECTION

PATENT NO.         : 8,436,141 B2                                                   Page 1 of 1
APPLICATION NO.    : 12/418222
DATED              : May 7, 2013
INVENTOR(S)        : María Inés Becker It is certified that error appears in the above-identified patent and that said Letters Patent is hereby corrected as shown below:

Title Page, Item (73)

In The Assignee:

Please correct the listed Assignees to reflect that "Fundación Ciencia y Tecnologia para el Desarrollo", SANTIAGO, CHILE is an Assignee along with Biosonda S.A., SANTIAGO, CHILE Signed and Sealed this
Fourteenth Day of January, 2014

Michelle K. Lee
*Deputy Director of the United States Patent and Trademark Office*